(12) United States Patent
Smith et al.

(10) Patent No.: US 11,471,679 B2
(45) Date of Patent: Oct. 18, 2022

(54) HEADPIECES AND IMPLANTABLE COCHLEAR STIMULATION SYSTEMS INCLUDING THE SAME

(71) Applicant: ADVANCED BIONICS AG, Staefa (CH)

(72) Inventors: James George Elcoate Smith, Santa Clarita, CA (US); Sung Jin Lee, Valencia, CA (US); Andreas Benedikt Brehm, Houston, TX (US)

(73) Assignee: Advanced Bionics AG, Staefa (CH)

( * ) Notice: Subject to any disclaimer, the term of this patent is extended or adjusted under 35 U.S.C. 154(b) by 84 days.

(21) Appl. No.: 16/754,126

(22) PCT Filed: Oct. 26, 2017

(86) PCT No.: PCT/US2017/058620
§ 371 (c)(1),
(2) Date: Apr. 6, 2020

(87) PCT Pub. No.: WO2019/083540
PCT Pub. Date: May 2, 2019

(65) Prior Publication Data
US 2020/0330777 A1  Oct. 22, 2020

(51) Int. Cl.
*A61N 1/36* (2006.01)
*A61N 1/372* (2006.01)
*H04R 25/00* (2006.01)

(52) U.S. Cl.
CPC ..... *A61N 1/36038* (2017.08); *A61N 1/37235* (2013.01); *H04R 25/606* (2013.01); *H04R 2225/51* (2013.01); *H04R 2225/67* (2013.01)

(58) Field of Classification Search
CPC ............ A61N 1/36038; A61N 1/37235; H04R 25/606; H04R 2225/51; H04R 2225/67; H04R 25/602; H04R 25/604
See application file for complete search history.

(56) References Cited

U.S. PATENT DOCUMENTS

| | | |
|---|---|---|
| 4,214,366 A | 7/1980 | Laban |
| 4,352,960 A | 10/1982 | Dormer et al. |
| 4,595,390 A | 6/1986 | Hakim et al. |
| 4,606,329 A | 8/1986 | Hough |
| 4,612,915 A | 9/1986 | Hough et al. |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |

(Continued)

FOREIGN PATENT DOCUMENTS

| | | |
|---|---|---|
| DE | 202006017662 U1 | 9/2007 |
| EP | 0241307 A2 | 10/1987 |

(Continued)

OTHER PUBLICATIONS

PCT International Search and Written Opinion dated May 24, 2018 for PCT App. Ser. No. PCT/US2017/058620.

(Continued)

*Primary Examiner* — Catherine M Voorhees
(74) *Attorney, Agent, or Firm* — Henricks Slavin LLP

(57) ABSTRACT

A headpiece including a housing, a headpiece magnet carried by the housing, and a headpiece antenna carried by the housing.

18 Claims, 13 Drawing Sheets

(56) References Cited

U.S. PATENT DOCUMENTS

| | | |
|---|---|---|
| 5,824,022 A | 10/1998 | Zilberman et al. |
| 5,945,762 A | 8/1999 | Chen et al. |
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling et al. |
| 7,091,806 B2 | 8/2006 | Zimmerling et al. |
| 7,190,247 B2 | 3/2007 | Zimmerling |
| 7,266,208 B2 | 9/2007 | Charvin et al. |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,027,735 B1* | 9/2011 | Tziviskos .......... A61N 1/36038 607/57 |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 10,532,209 B2 | 1/2020 | Lee et al. |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 | 11/2020 | Lee et al. |
| 11,097,095 B2 | 8/2021 | Smith et al. |
| 11,287,495 B2 | 3/2022 | Smith et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0015155 A1 | 1/2006 | Charvin et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0192968 A1 | 8/2008 | Ho et al. |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0336447 A1 | 11/2014 | Bjorn et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0094521 A1 | 4/2015 | Neuman et al. |
| 2015/0100109 A1 | 4/2015 | Feldman et al. |
| 2015/0112407 A1 | 4/2015 | Hartley et al. |
| 2015/0265842 A1 | 9/2015 | Ridker |
| 2015/0320523 A1 | 11/2015 | Way et al. |
| 2015/0367126 A1 | 12/2015 | Smyth |
| 2015/0382114 A1 | 12/2015 | Andersson et al. |
| 2016/0008596 A1 | 1/2016 | Gibson et al. |
| 2016/0023006 A1* | 1/2016 | Ridler ................ A61N 1/0541 607/57 |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1* | 7/2016 | Heerlein .............. H04R 25/554 |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1* | 8/2017 | Lee .................... A61N 1/36038 |
| 2017/0347208 A1 | 11/2017 | Jurkiewicz |
| 2018/0028818 A1 | 2/2018 | Anderson et al. |
| 2018/0056084 A1 | 3/2018 | Alam |
| 2018/0110985 A1 | 4/2018 | Walter |
| 2018/0110986 A1 | 4/2018 | Lee |
| 2018/0133486 A1 | 5/2018 | Smith |
| 2018/0146308 A1 | 5/2018 | Leigh et al. |
| 2018/0160241 A1* | 6/2018 | Gustafsson ......... H04R 25/606 |
| 2018/0160242 A1 | 6/2018 | Sriskandarajah |
| 2018/0185634 A1 | 7/2018 | Smyth |
| 2018/0249262 A1 | 8/2018 | Santek |
| 2018/0270591 A1 | 9/2018 | Kennes |
| 2018/0296826 A1 | 10/2018 | Lee et al. |
| 2018/0303602 A1 | 10/2018 | Leigh |
| 2018/0304078 A1 | 10/2018 | Crawford et al. |
| 2018/0369586 A1 | 12/2018 | Lee et al. |
| 2019/0015662 A1 | 1/2019 | Raje et al. |
| 2019/0046797 A1 | 2/2019 | Calixto et al. |

(56) References Cited

U.S. PATENT DOCUMENTS

| | | | |
|---|---|---|---|
| 2019/0053908 A1 | 2/2019 | Cook et al. | |
| 2019/0076649 A1* | 3/2019 | Lee | A61N 1/36038 |
| 2019/0255316 A1 | 8/2019 | Lee et al. | |
| 2019/0298417 A1 | 10/2019 | Barrett et al. | |
| 2020/0114151 A1 | 4/2020 | Smith et al. | |
| 2020/0230422 A1 | 7/2020 | Gibson et al. | |
| 2020/0238088 A1 | 7/2020 | Smith et al. | |
| 2020/0391023 A1 | 12/2020 | Lee et al. | |
| 2021/0046311 A1 | 2/2021 | Brehm et al. | |
| 2021/0106815 A1 | 4/2021 | Smith et al. | |
| 2021/0156934 A1 | 5/2021 | Smith et al. | |
| 2021/0299456 A1 | 9/2021 | Smith et al. | |
| 2021/0316136 A1 | 10/2021 | Smith et al. | |
| 2021/0339021 A1 | 11/2021 | Brehm et al. | |

FOREIGN PATENT DOCUMENTS

| | | |
|---|---|---|
| EP | 2117489 B1 | 5/2010 |
| EP | 2853287 A1 | 4/2015 |
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004004416 A1 | 1/2004 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2012010195 A1 | 1/2012 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018217187 A1 | 11/2018 |
| WO | WO2019083540 A1 | 5/2019 |
| WO | WO2019160555 A1 | 8/2019 |
| WO | WO2020092185 A1 | 5/2020 |
| WO | WO2021201845 A1 | 10/2021 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.

U.S. Appl. No. 17/073,322, filed Oct. 17, 2020.
U.S. Appl. No. 17/008,291, filed Aug. 31, 2020.
U.S. Appl. No. 16/610,502, filed Nov. 2, 2019.
U.S. Appl. No. 16/499,311, filed Sep. 29, 2019.
U.S. Appl. No. 16/754,126, filed Apr. 6, 2020.
U.S. Appl. No. 16/966,885, filed Aug. 1, 2020.
U.S. Appl. No. 16/966,885, filed Aug. 1, 2020, 20210046311 A1.
U.S. Appl. No. 16/499,311, filed Sep. 29, 2019, 20210106815 A1.
U.S. Appl. No. 17/355,225, filed Jun. 23, 2021.
U.S. Appl. No. 17/335,161, filed Jun. 1, 2021.
U.S. Appl. No. 17/346,343, filed Jun. 14, 2021.
U.S. Appl. No. 16/610,502, filed Nov. 2, 2019, 20210156934 A1.
U.S. Appl. No. 15/568,469, filed Oct. 21, 2017, 20180110985 A1.
U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aug. 31, 2020, 20200391023 A1.
U.S. Appl. No. 16/610,502, filed Nov. 2, 2019, U.S. Pat. No. 11,287,495.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, 20210316136 A1.
U.S. Appl. No. 16/603,868, filed Oct. 9, 2019, 20200114151 A1.
U.S. Appl. No. 16/754,126, filed Apr. 6, 2020, 20200330777 A1.
U.S. Appl. No. 17/335,161, filed Jun. 1, 2021, 20210339021 A1.
U.S. Appl. No. 17/346,343, filed Jun. 14, 2021, 20210299456 A1.
U.S. Appl. No. 17/499,813, filed Oct. 12, 2021.

* cited by examiner

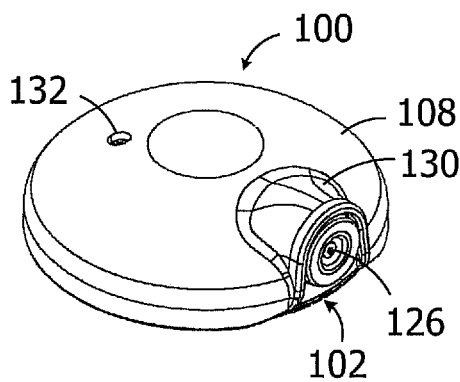
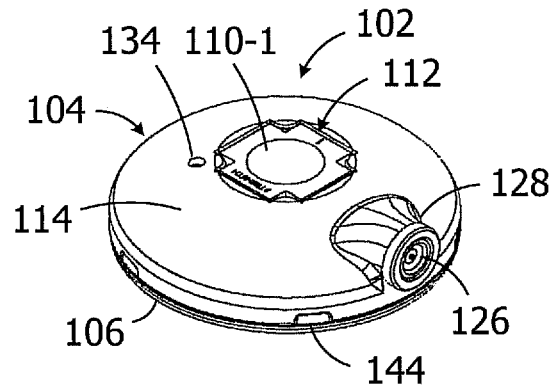
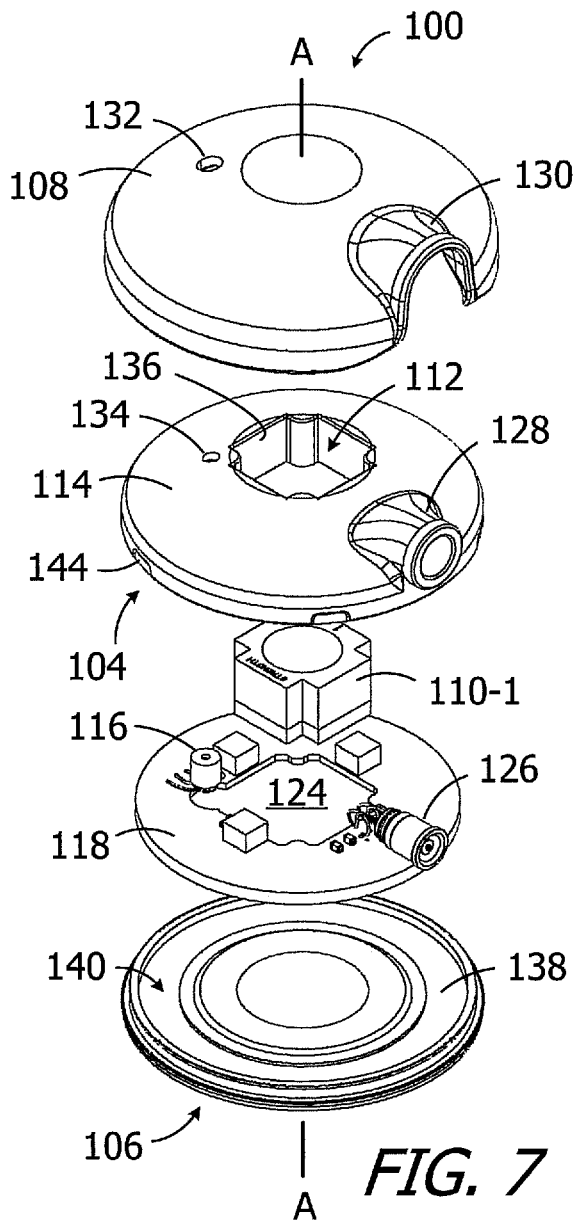

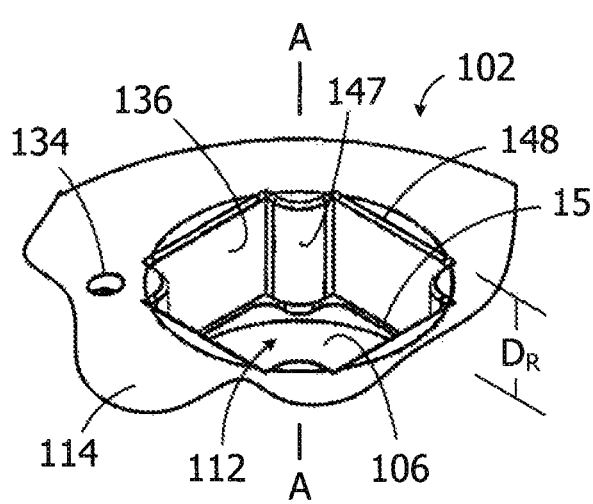
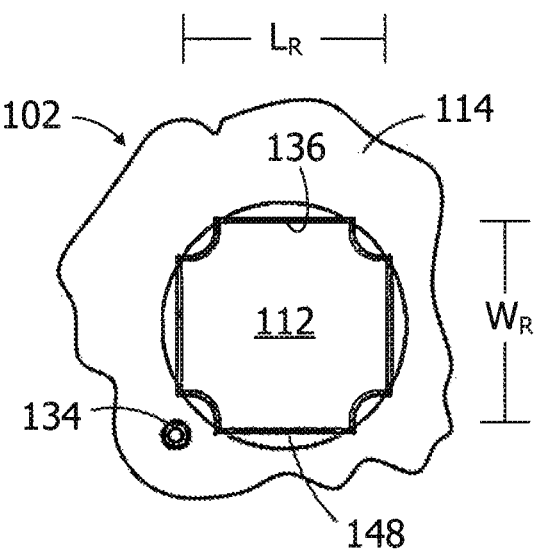
FIG. 9     FIG. 10
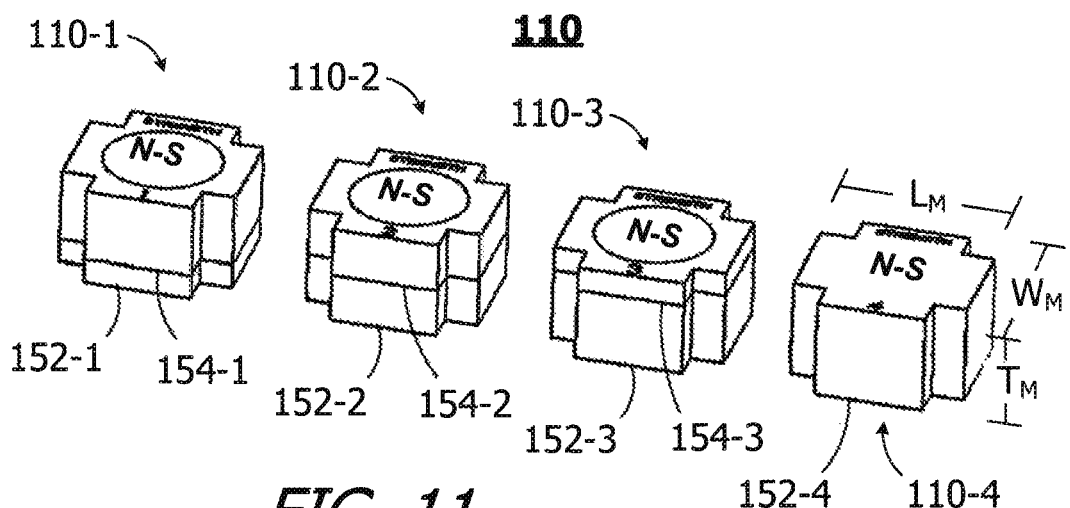
FIG. 11
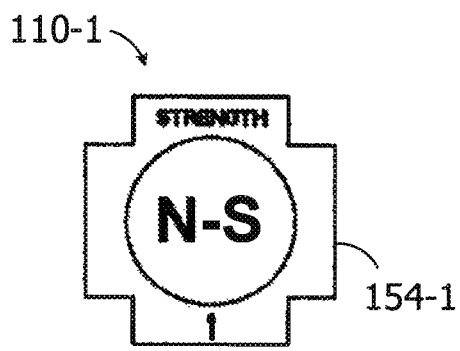  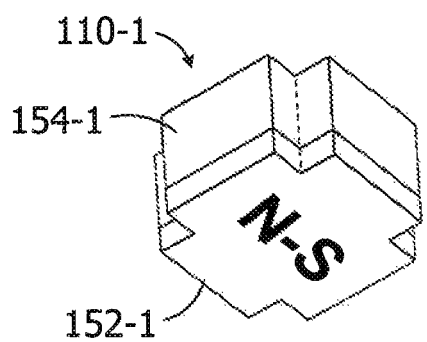
FIG. 12     FIG. 13

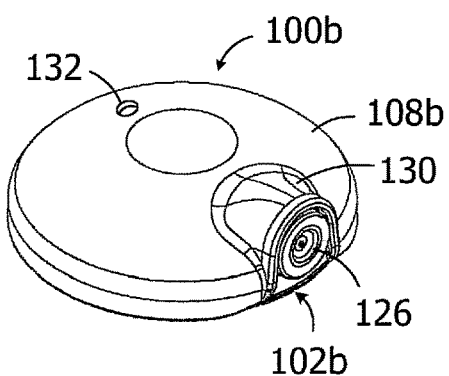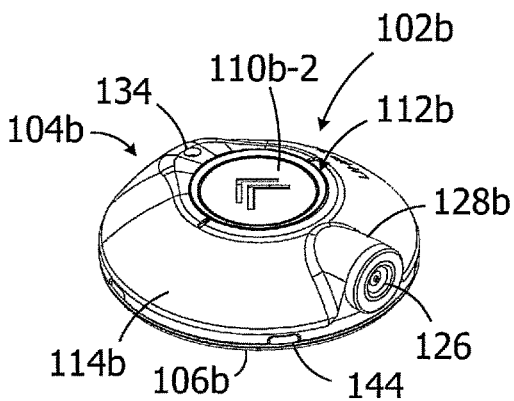
FIG. 24    FIG. 25
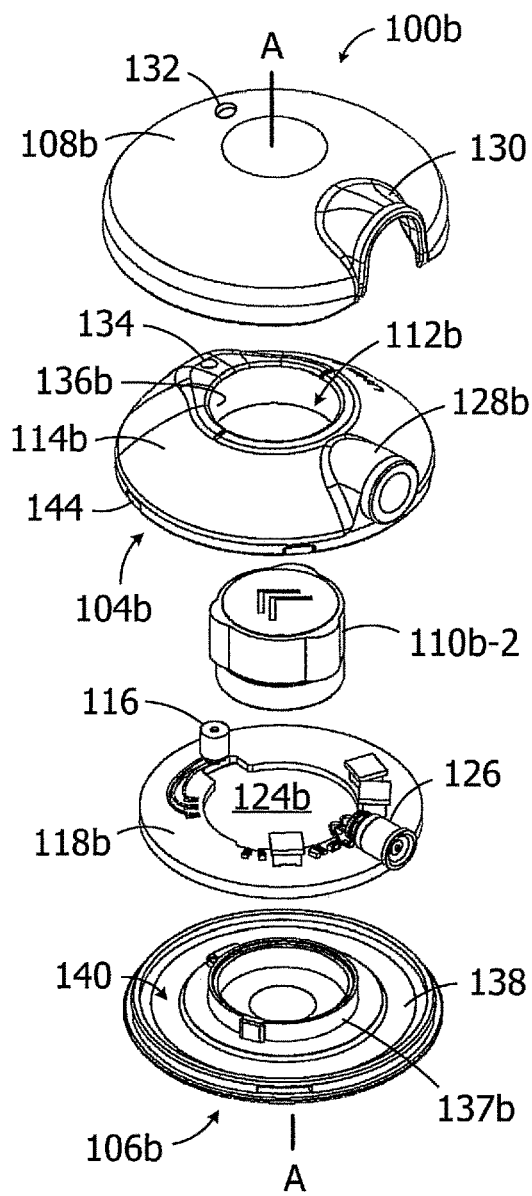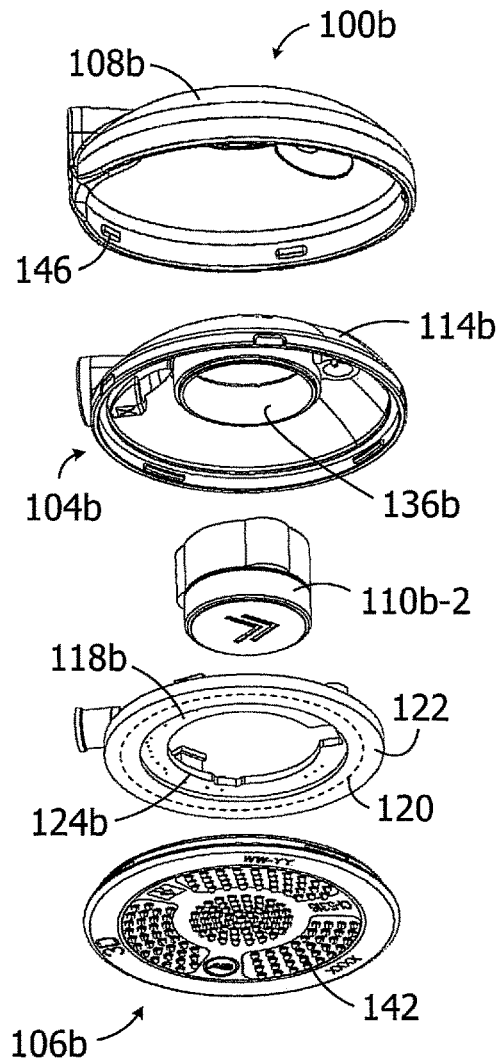
FIG. 26    FIG. 27

32 housing
34 antenna
36 magnet
38 cochlear lead
40 printed circuit board 102 housing
110-1 magnet
108 removable cap
118 printed circuit board
120 antenna
126 connector

HEADPIECES AND IMPLANTABLE COCHLEAR STIMULATION SYSTEMS INCLUDING THE SAME

CROSS-REFERENCE TO RELATED APPLICATIONS

This application is the U.S. National Stage of PCT App. Ser. No. PCT/US2017/058620, filed Oct. 26, 2017.

BACKGROUND

1. Field

The present disclosure relates generally to implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. The headpiece and the cochlear implant may include respective magnets (or respective pluralities of magnets) that are attracted to one another, thereby retaining the headpiece on the head and maintaining the position of the headpiece transmitter on the head over the implant receiver. The skin and subcutaneous tissue that separates the headpiece magnet and implant magnet is sometimes referred to as the "skin flap."

One example of a conventional headpiece is the headpiece 10 illustrated in FIGS. 1-4. The headpiece 10 includes a housing 12, in which components such as a microphone and a printed circuit board that carries an antenna 14 and other electronic components are located, and a removable cap 16 that may be secured to the housing. An electrical connector 18 connects the circuit board to a sound processor (e.g., a BTE sound processor) by way of a cable 20. A plurality of axially magnetized headpiece magnets 22 (note axis A), or a combination of magnets and non-magnetic spacers, are located within a receptacle 24 that extends to the top wall 26 of the housing 12. The cap 16 keeps the magnets 22 and spacers (if any) within the receptacle 24, and can be removed and reattached so that the respective numbers of magnets and spacers can be modified to adjust the magnetic strength of the headpiece. The headpiece 10 may be used in conjunction with a cochlear implant 30 that includes a housing 32, an antenna 34, an axially magnetized positioning magnet 36, and a cochlear lead 38.

The proper retention of the headpiece 10 on the skull and over the cochlear implant 30 depends on the normal retention force NRF and the lateral retention force LRF. The normal retention force NRF is a function of the strength of the headpiece and implant magnets 18 and 30 as well as the thickness of the skin flap and hair (if any), while the lateral retention force LRF is a function of the normal retention force NRF and the coefficient of friction between the headpiece and the associated head surface. Pressure on the skin flap can result in discomfort and tissue necrosis when the normal retention force NRF is too high, while the headpiece will not be retained when the normal retention force NRF is too low.

Certain headpieces, including the headpiece illustrated in FIGS. 1-4, are configured in such a manner that the magnetic strength associated therewith may be adjusted as necessary for each patient. The magnetic strength of the headpiece 10 is determined by the number of the magnets 22 placed into the receptacle 24. The present inventors have determined that the headpiece 10 is susceptible to improvement. For example, the magnets 22 have a standard disk shape and, accordingly, a patient (or other non-audiologist) may substitute stronger similarly sized disk-shaped magnets for the magnets 22 in an attempt to improve retention. Such attempts are misguided because the resulting additional pressure on the skin may cause tissue necrosis. This issue is especially concerning in the case of pediatric patients and their parents, because the skin flaps of pediatric patients are very thin (i.e., about 2-4 mm thick). Accordingly, the present inventors have determined that it would be beneficial to prevent the use of any magnets other than those which are specifically intended for use with the associated headpiece.

Other headpieces are provided with magnet systems that include a plurality of magnets of different strengths that can be individually mounted, i.e., mounted only one at a time, within the associated headpiece. Such magnets sometimes have locking features that mate with the headpiece in response to, for example, rotation of the magnet relative to the headpiece. The present inventors have determined that the manner in which the magnets are connected to the associated headpiece is somewhat limiting, and that different methods of connecting the magnets would result in a greater number of magnetic strength options with the same number of magnets.

Still other issues identified by the present inventors relate to the use of diametrically magnetized magnets in cochlear implants. For example, were one to stack a plurality of diametrically magnetized magnets within a receptacle in a manner similar to the magnets 22 in FIG. 3, the N poles would align with the S poles of adjacent magnets within the receptacle, which is magnetically inefficient as compared to a stack with all of the magnets oriented in the same N-S direction. Another issue is associated with the fact that, for a given normal retention force NRF, the lateral retention force LRF is maximized when the N-S axis aligned with the gravitational direction G. Given that headpieces are typically worn with the headpiece cable extending downwardly in the gravitational direction G (FIG. 4), some conventional headpieces fixedly align the N-S direction of the headpiece magnet, which can be problematic for persons who do no wear their headpiece in the typical manner.

SUMMARY

A cochlear implant headpiece in accordance with one of the present inventions includes a housing including a bottom wall and a magnet receptacle and defining an axis that extends through the magnet receptacle in a direction perpendicular to the bottom wall, the magnet receptacle defining a non-circular shape in a plane perpendicular to the axis, a headpiece magnet, defining the non-circular shape in a plane perpendicular to the axis, removably located within the magnet receptacle, and a headpiece antenna carried by the housing. The present inventions also include cochlear stimulation systems with a sound processor and/or a cochlear implant in combination with such a headpiece.

A cochlear implant headpiece in accordance with one of the present inventions includes a housing including a bottom wall and a magnet receptacle, a headpiece magnet, including a magnetic member and a compressible non-magnetic member permanently secured to the magnetic member, removably located within the magnet receptacle, and a headpiece antenna carried by the housing. The present inventions also include cochlear stimulation systems with a sound processor and/or a cochlear implant in combination with such a headpiece.

A magnet kit in accordance with one of the present inventions includes a first magnet apparatus having a first magnetic strength and including a first magnetic member defining a N-S magnetization direction and a cruciform shape in a plane parallel to the N-S magnetization direction, and a second magnet apparatus having a second magnetic strength, which is greater than the first magnetic strength, and including a second magnetic member defining a N-S magnetization direction and a cruciform shape in a plane parallel to the N-S magnetization direction.

A magnet kit in accordance with one of the present inventions includes a first magnet apparatus having a first magnetic strength and including a first magnetic member and a first compressible non-magnetic member permanently secured to the first magnetic member, and a second magnet apparatus having a second magnetic strength, which is greater than the first magnetic strength, and including a second magnetic member and a second compressible non-magnetic member permanently secured to the second magnetic member.

There are a variety of advantages associated with such headpieces, systems and kits. By way of example, but not limitation, some or all of the present inventions decrease the likelihood that a stronger similarly sized magnets may be employed in place of (or stacked along with) the intended magnets, increase the number of magnetic strength options associated with a given number of magnets within a magnet set, are well suited for use with diametrically magnetized cochlear implant magnets, and are well suited for persons who do no wear their headpiece in the typical manner relative to the gravitational direction.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 5 is a perspective view of a headpiece in accordance with one embodiment of a present invention.

FIG. 6 is a perspective view of a portion of the headpiece illustrated in FIG. 5.

FIG. 7 is an exploded perspective view of the headpiece illustrated in FIG. 5.

FIG. 8 is an exploded perspective view of the headpiece illustrated in FIG. 5.

FIG. 9 is a perspective view of a portion of the headpiece illustrated in FIG. 5.

FIG. 10 is a top view of a portion of the headpiece illustrated in FIG. 5.

FIG. 11 is a perspective view of a magnet system in accordance with one embodiment of a present invention.

FIG. 12 is a top view of one of the magnets illustrated in FIG. 11.

FIG. 13 is a perspective view of one of the magnets illustrated in FIG. 11.

FIG. 24 is a perspective view of a headpiece in accordance with one embodiment of a present invention.

FIG. 25 is a perspective view of a portion of the headpiece illustrated in FIG. 24.

FIG. 26 is an exploded perspective view of the headpiece illustrated in FIG. 24.

FIG. 27 is an exploded perspective view of the headpiece illustrated in FIG. 24.

DETAILED DESCRIPTION OF THE EXEMPLARY EMBODIMENTS

Figure 1:
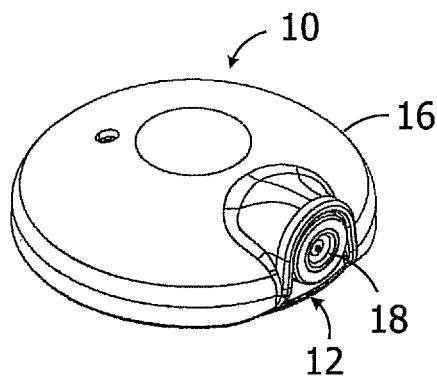
FIG. 1 is a perspective view of a conventional headpiece.
Figure 2:
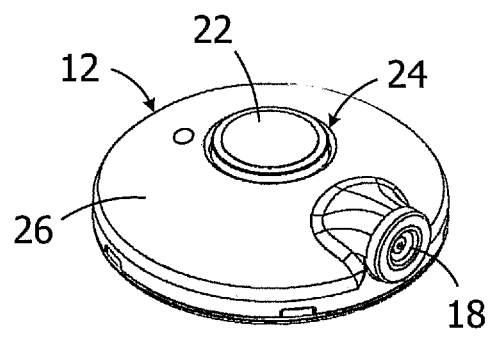
FIG. 2 is a perspective view of a portion of the headpiece illustrated in FIG. 1.
Figure 3:
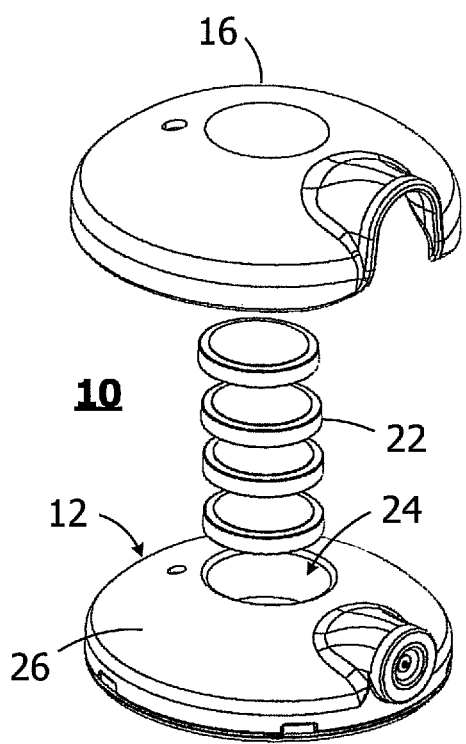
FIG. 3 is an exploded perspective view of the headpiece illustrated in FIG. 1.
Figure 4:
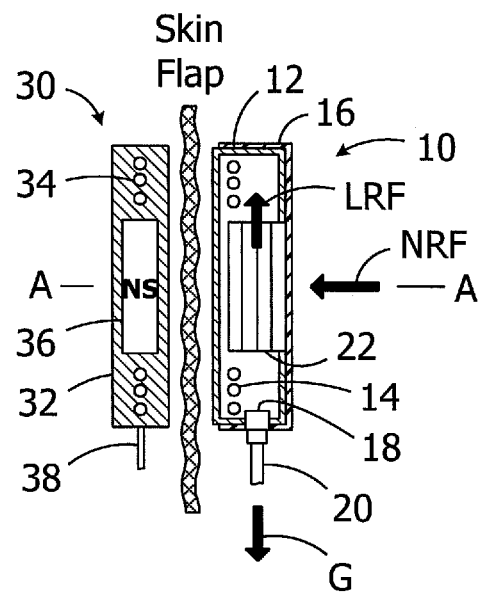
FIG. 4 is a simplified side, section view of a cochlear implant and the headpiece illustrated in FIG. 1.

The following is a detailed description of the best presently known modes of carrying out the inventions. This description is not to be taken in a limiting sense, but is made merely for the purpose of illustrating the general principles of the inventions.

An exemplary headpiece in accordance with at least one of the present inventions is illustrated in FIGS. 5-8 and is generally represented by reference numeral 100. The exemplary headpiece 100 may include a housing 102, with a main portion 104 and a cover 106, and a removable cap 108 that may be secured to the housing. A single headpiece magnet apparatus (also referred to herein as a "magnet") 110-1 is located within a receptacle 112 that extends to the top wall 114 of the main portion 104. The cap 108 keeps the magnet 110-1 within the receptacle 112, and can be removed and reattached so that the magnet can be removed and replaced. As is discussed in greater detail below with reference to FIGS. 9-13, the receptacle 112 is configured in such a manner that a conventional disk-shaped magnet, i.e., a magnet that has a circular cross-section in a plane perpendicular to the axis A, must be relatively small to fit into the receptacle, thereby reducing the likelihood that a person can increase the magnetic strength beyond the recommended level with unauthorized magnets. The magnet 110-1 has a size and shape corresponding to that of the receptacle 112 (FIG. 6). As such, the presence of the magnet 110-1 in the receptacle 112 prevents additional magnets (regardless of configuration) from being inserted into the receptacle, thereby preventing the unauthorized use of an additional magnet. The magnet 110-1 may also be part of a magnet system that includes a plurality of similar-shaped magnets having different magnetic strengths, as is discussed below with reference to FIGS. 11-13.

The internal volume of the exemplary housing 102 includes a microphone 116 and a printed circuit board (PCB) 118 which carries the microphone and various other headpiece electronic components on one side. The other side of the PCB 118 includes an antenna 120 within an annular protective covering 122 (FIG. 8). In other implementations, the antenna may be carried by the cover 106. The PCB 118 also includes an aperture 124 through which the receptacle 112 extends. A connector 126, such as a RF connector, is connected to the PCB 118 and extends through a tube 128 on the housing main portion 104. The exemplary cap 108 has a hood 130 to accommodate the connector 126 and tube 128. The housing 102 and cap 108 also include microphone ports 132 and 134 that are aligned with the microphone 116. A shield (not shown) may be positioned over the port 132 on the inner surface of the cap 108.

In the illustrated implementation, the housing main portion 104 includes a plurality of walls 136 that define the sides of the receptacle 112. The housing cover 106 includes a bottom wall 138, which forms the bottom of the receptacle 112, and an annular indentation 140 for the antenna's protective covering 122. The bottom (or "exterior") surface of the bottom wall 138 may be concave or flat, and may include a plurality of protrusions 142. The housing 102 and cap 108 may be attached to one another with any suitable instrumentalities. In the illustrated implementation, the housing main portion 104 includes a plurality of latch indentations 144 that are engaged by a corresponding plurality of latches 146 on the cap 108 when the cap is positioned over the housing 102 in the manner illustrated in FIG. 5.

As illustrated in FIGS. 9 and 10, the exemplary receptacle 112 has a cruciform shape in a plane perpendicular to the axis A that extends through receptacle in a direction perpendicular to the bottom wall 138. Other suitable shapes include, but are not limited to, triangle, ellipses and other non-circular shapes in a plane perpendicular to the axis A that will limit the size of circular magnets that can be inserted into the receptacle. The exemplary receptacle 112 is defined by the aforementioned cover 106 and planar walls 136, as well as the curved corner walls 147. The walls 136 and 147 include respective top ends 148 that are adjacent to the top wall 114 of the housing main portion 104 and respective bottom ends 150 that are adjacent to the housing cover 106. The receptacle 112 also defines a depth $D_R$, which is this distance from the top end 148 to the bottom end 150, a length $L_R$ and a width $W_R$. Although the length $L_R$ and width $W_R$ are the same in the illustrated embodiment, they may be different in other embodiments.

Turning to FIGS. 11-13, the exemplary magnet 110-1 is one magnet in a multiple magnet system 110 that also includes magnets 110-2, 110-3 and 110-4. The magnets in the system 110 are identical in shape and size, but have different magnetic strengths. The magnets in the system 110 also have the same non-circular shape as the receptacle 112 and, as a result, the magnets are not rotatable relative to the receptacle when in the receptacle. In the exemplary implementation, the magnets in the system 110 each have a cruciform shape that is similar to that of receptacle 112 and each have the same thickness $T_M$, length $L_M$, width $W_M$ and volume. Although the length $L_M$ and width $W_M$ are the same in the illustrated embodiment, they may be different in other embodiments. The length $L_M$ and width $W_M$ of the magnets 110-1 to 110-4 may be identical to, or are at least substantially identical to (i.e., up to 3% less than), the length $L_R$ and width $W_R$ of the receptacle. The thickness $T_M$ may be at least 90% of the receptacle depth $D_R$ and, in the illustrated implementation, is at least substantially identical to depth $D_R$ (i.e., ±5%). In those instances where the magnet thickness $T_M$ is greater than the receptacle depth $D_R$ (up to 10% greater), the inner surface of the cap 108 may have a small recess (not shown) that can accommodate the portion of the magnet that extends beyond the receptacle 112.

There are a variety of ways to vary the strength from one magnet to another in a magnet system, such as magnet system 110, where the magnets are the same overall size and shape. For example, the magnets 110-1 to 110-4 may be formed from materials with different magnetic strengths. Alternatively, or in addition, portions of the three weaker magnets may be removed (e.g., by drilling differently sized holes through the magnets). In the illustrated implementation, all but one of the magnets is a two-part structure that includes a respective magnetic member 152-1 to 152-3 and a respective non-magnetic member 154-1 to 154-3. In the illustrated implementation, the magnetic and non-magnetic members have the same non-circular shape (e.g., cruciform shape) in respective planes perpendicular to the axis A. The magnet 110-4 is formed entirely from magnetic material and, accordingly, consists solely of a magnetic member 152-4. The strength of the magnets 110-1 to 110-3 may be varied by varying the relative thicknesses of the magnetic members 152-1 to 152-3 and non-magnetic member 154-1 to 154-3. For example, the magnetic strength of the magnet 110-2 is greater than the magnet 110-1. Although the overall thickness $T_M$ of the magnets 110-1 and 110-2 is the same, the thickness of the magnetic member 152-2 is greater than the thickness of the magnetic member 152-1, while the thickness of the non-magnetic member 154-2 is less than the thickness of the magnetic member 152-1.

In the illustrated embodiment, the magnetic members 152-1 to 152-3 are permanently secured to the non-magnetic member 154-1 to 154-3 through the use of adhesive or other suitable instrumentalities. As used here, the phrase "permanently secured" means that, once connected, the magnetic members will remain attached to the non-magnetic members under normal use conditions, and cannot be separated from one another without destruction of the magnetic members, the non-magnetic members and/or the instrumentality that secures the two to one another. Suitable materials for the magnetic members include, but are not limited to neodymium, while suitable materials for the non-magnetic members include, but are not limited to, plastics and other relatively rigid and lightweight materials.

The N-S magnetization direction of the magnetic members 154-1 to 154-4 will depend on the intended application. In those instances where the cochlear implant includes an axially magnetized positioning magnet, the N-S magnetization direction of the magnetic members 154-1 to 154-4 may be in the thickness direction that aligns with the axis A (FIG. 9) when a magnet member is within the receptacle 112. In the illustrated embodiment, the N-S magnetization direction of the magnetic members 154-1 to 154-4 may be in the length (or width) direction that is perpendicular to the axis A (FIGS. 9 and 14) and, therefore, perpendicular to the axis A, when a magnet member is within the receptacle 112.

In at least some implementations, the magnets within a magnet system may include visible and/or tactile indicia that identify the relative magnet strength and/or the N-S magnetization direction of the magnet. For example, the exemplary magnets 110-1 to 110-4 may include indicia that in the form of numbers on the top surfaces (in the illustrated orientation) of the non-magnetic members 154-1 to 154-3 that are representative of the relative magnet strengths, i.e., "1" being lowest and "4" being highest. Alternatively, or in addition, the non-magnetic members 154-1 to 154-3 may be different colors, with each color corresponding to a relative magnetic strength. The exemplary magnets 110-1 to 110-4 also include "N-S" indicia on the bottom surfaces of the magnetic members 152-1 to 152-4 and the top surfaces non-magnetic members 154-1 to 154-4.

Figure 14:
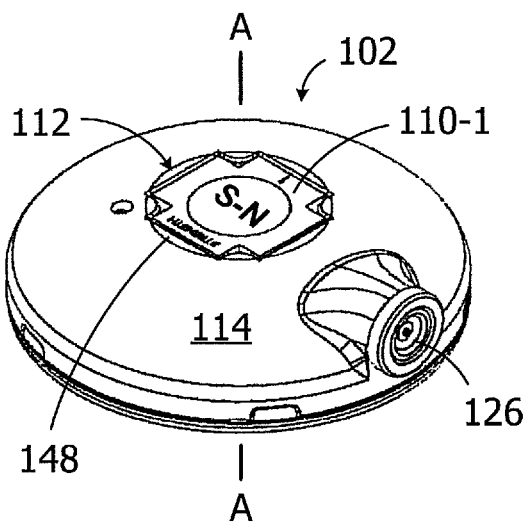
FIG. 14 is a perspective view of a portion of the headpiece illustrated in FIG. 5.
Figure 15:
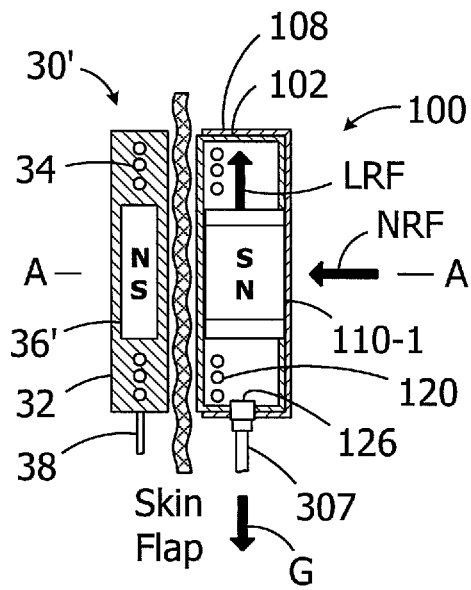
FIG. 15 is a simplified side, section view of a cochlear implant and the headpiece illustrated in FIG. 5.

There are a variety of advantages associated with the exemplary headpiece 100 and magnet system 110. For example, and as illustrated in FIG. 14, magnet 110-1 occupies the entire volume (or essentially the entire volume) of the receptacle 112, as do the other magnets 110-2 to 110-4, thereby preventing the insertion of additional magnets into the receptacle. The headpiece 100 is also especially useful with cochlear implants, such as the cochlear implant 30' illustrated in FIG. 15, that include a rotatable diametrically magnetized positioning magnet 36' (or the magnet apparatus described below with reference to FIGS. 15A-15D) in addition to a housing 32, antenna 34, and cochlear lead 38. The cochlear implant 30' also includes a printed circuit board 40 (FIG. 45) with a stimulation processor that converts the stimulation data into stimulation signals that stimulate the electrodes of the lead 38. The respective orientations of the receptacle 112 and the N-S magnetization direction of the magnets in the system 110 allows the user to align the N-S magnetization direction with the connector 126, as is illustrated in FIG. 14. As a result, the lateral retention force LRF is maximized when the headpiece 100 is worn with a cable 307 (discussed below with reference to FIG. 45) that is connected to the connector 126 extends downwardly in the gravitational direction G (as shown) because the N-S magnetization direction of the headpiece magnet 110-1 and rotatable implant magnet 36' will be aligned with the gravitational direction G.

The present headpieces may also be used in conjunction with cochlear implants that include a magnet apparatus which has a plurality of diametrically magnetized magnets as well as a N-S magnetization direction that rotates into alignment with the associated headpiece magnet. To that end, and referring to FIGS. 15A-15D, the exemplary MRI-compatible magnet apparatus 36" may be used in place of the magnet 36' in the implant 30'. The magnet apparatus 36" includes a case 52, with base 54 and a cover 56, a magnet frame 58, and a plurality of elongate diametrically magnetized magnets 60 within the frame that define a N-S direction. The exemplary case 52 is disk-shaped and defines a central axis A, which is also the central axis of the magnet frame 58. The magnet frame 58 is freely rotatable relative to the case 52 about the central axis A over 360°. The magnets 60 rotate with the magnet frame 58 about the central axis A. Each magnet 60 is also freely rotatable relative to the magnet frame 58 about its own longitudinal axis A2 over 360°. The longitudinal axes A2 are parallel to one another and are perpendicular to the central axis A.

There are four elongate diametrically magnetized magnets 60 in the exemplary magnet apparatus 36". Two of the otherwise identical magnets 60 are relatively long and two are relatively short in order to efficiently utilize the available volume within the case 52. As such, the magnets 60 together define a cruciform shape similar to headpiece magnet 110-1. The exemplary magnets 60 are circular in a cross-section, have rounded corners 62, and are located within low friction tubes 64. The exemplary magnet frame 58 includes a disk 66 and a magnet receptacle 68 that extends completely through the disk. The magnet receptacle 68 is configured to hold all of the magnets 60 (four in the illustrated embodiment) and includes a relatively long portion and two relatively short portions. The inner surfaces of the case 52 and/or the surfaces of the frame 58 may be coated with a lubricious layer.

Given the ability of each magnet 60 of the apparatus 36″ illustrated in FIGS. 15A-15D to freely rotate about its longitudinal axis A2, the magnets 60 align with one another in the N-S direction in the absence of a relatively strong external magnetic field (e.g., an MRI magnetic field), and the at rest N-S orientation of the magnets 60 will be perpendicular to the central axis A. So oriented, the magnetic fields of the diametrically magnetized magnets 60 are aligned with the magnetic field of a headpiece magnet, such as a headpiece magnet 110-1, with the same N-S magnetization direction. It should also be noted here that the magnetic field of the headpiece magnets disclosed herein will not be strong enough to cause the magnets 60 to rotate out of the illustrated at rest N-S orientation. Although the frame 58 will rotate as necessary, the magnets 60 will remain in the N-S orientation illustrated in FIG. 15D and will continue to function as a magnetic unit in the presence of a headpiece magnet. Additional details concerning the magnet apparatus illustrated in FIGS. 15A-15D (and other magnet apparatus) may be found in U.S. Pat. Pub. No. 2017/0239476, which is incorporated herein by reference in its entirety.

Figure 16:
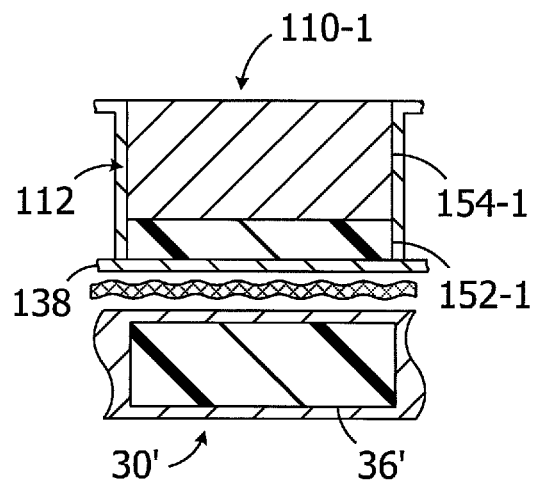
FIG. 16 is a simplified side, section view of portions of a cochlear implant and the headpiece illustrated in FIG. 5.
Figure 17:
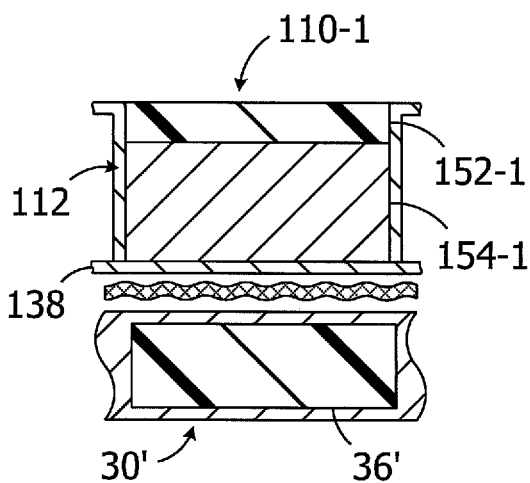
FIG. 17 is a simplified side, section view of portions of a cochlear implant and the headpiece illustrated in FIG. 5.
Figure 15A:
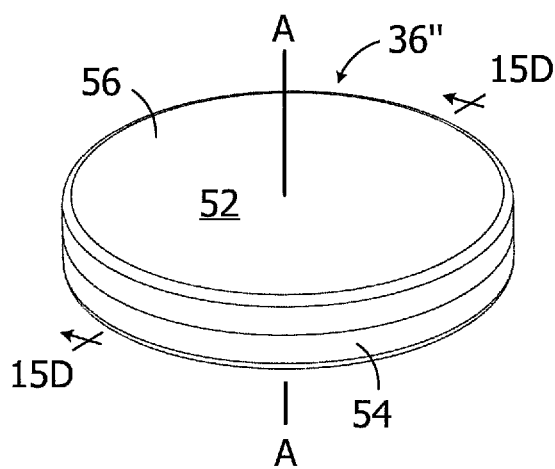
FIG. 15A is a perspective view of an exemplary implant magnet apparatus.
Figure 15B:
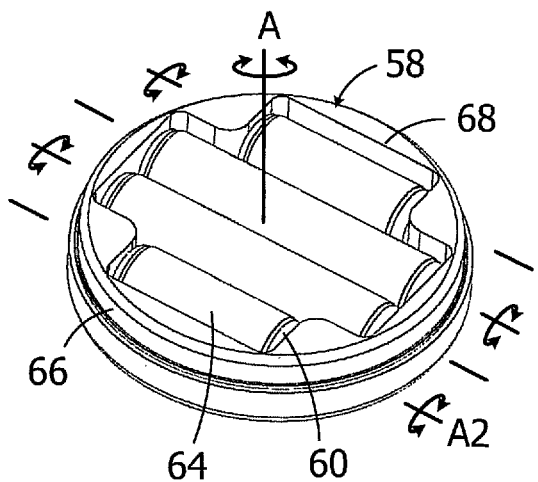
FIG. 15B is a perspective view of a portion of the implant magnet apparatus illustrated in FIG. 15A.
Figure 15C:
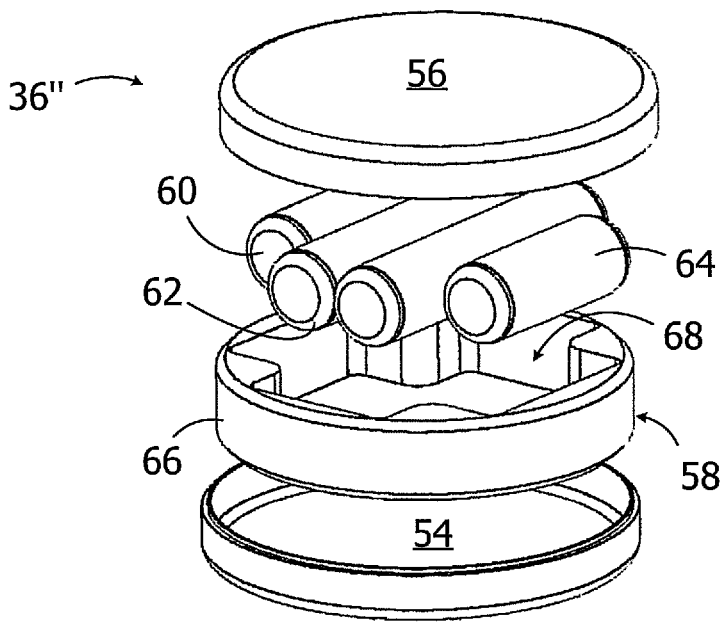
FIG. 15C is an exploded view of the implant magnet apparatus illustrated in FIG. 15A.
Figure 15D:
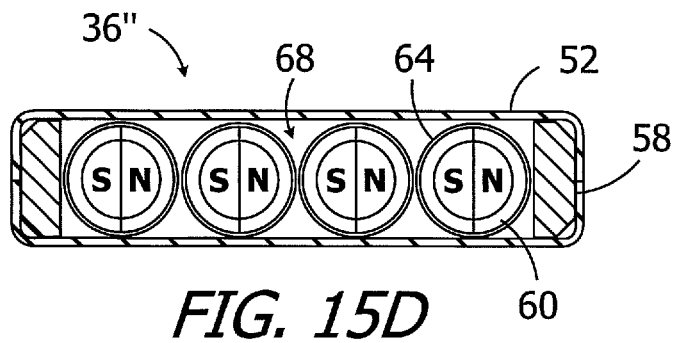
FIG. 15D is a section view take along line 15D-15D in FIG. 15A.

Turning to FIGS. 16 and 17, and due to their respective configurations, the number of magnetic strength options provided by the exemplary headpiece 100 and magnet system 110 is greater than the number of magnets in the system. In particular, the magnetic attraction force between a headpiece magnet and an implant magnet is a function of the magnetic strength of the magnets and the distance between the magnets. The magnets 110-1 to 110-3, each of which has a different strength, may be inserted with the magnetic member 152-1 to 152-3 facing the implant magnet 36′ (e.g., magnetic member 152-1 in FIG. 16), or with the associated non-magnetic member 154-1 to 154-3 facing the implant magnet (e.g., non-magnetic member 154-1 in FIG. 17). Put another way, the magnets 110-1 to 110-3 may be inserted into the receptacle 112 in such a manner that the non-magnetic member 154-1 to 154-3 is between the associated magnetic member 152-1 to 152-3 and the bottom wall 138, or in such a manner that the non-magnetic member is not between the associated magnetic member and the bottom wall. The user can, therefore, select either of two possible magnetic member to implant magnet distances for each of the magnets 110-1 to 110-3 depending upon the insertion orientation of the magnet. The magnet 110-4, which lacks a non-magnetic member, does not have this functionality. Accordingly, each of the magnets 110-1 to 110-3 is capable of creating two different magnetic attraction forces with the same implant magnet, as compared to conventional magnet systems whose magnets are limited to a single insertion orientation.

The cruciform shape of the present magnets 110-1 to 110-4 may also be used to provide a more volumetrically efficient headpiece, as compared to headpieces that employ disk-shaped magnets with circular cross-sections. In particular, relatively tall components on the PCB 118 (such as the microphone 116) may be positioned closer to the center of the headpiece, which facilitates the use of thinner housings.

Figure 18:
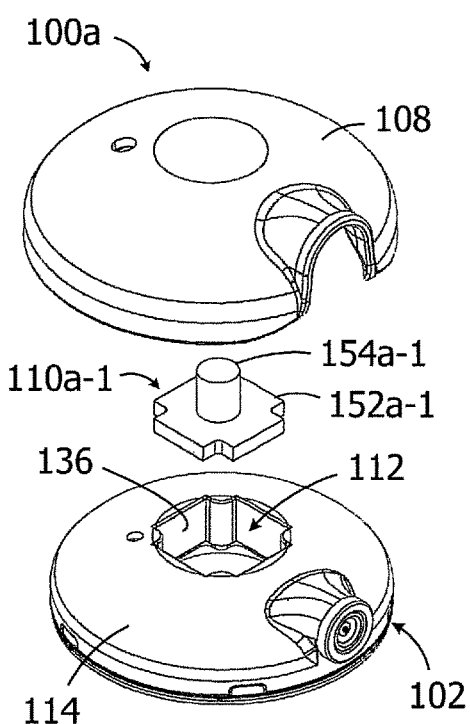
FIG. 18 is an exploded perspective view of a headpiece in accordance with one embodiment of a present invention.
Figure 19:
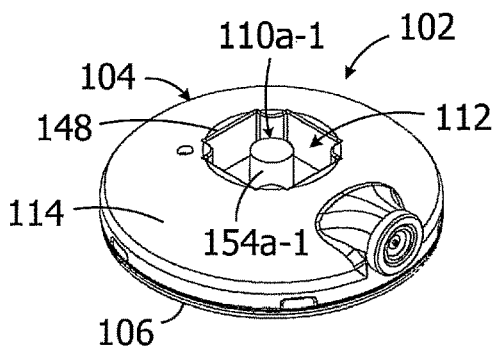
FIG. 19 is a perspective view of a portion of the headpiece illustrated in FIG. 18.

The present inventions are not limited to the exemplary magnet configuration illustrated in FIGS. 5-17. By way of example, the headpiece 100a illustrated in FIGS. 18 and 19 is substantially similar to the headpiece 100 and similar elements are represented by similar reference numerals. For example, the headpiece 100a includes a housing 102 with the above-described internal components, a receptacle 112, and a removable cap 108 that may be secured to the housing to cover the receptacle. The headpiece 100a also includes a single headpiece magnet apparatus (also referred to herein as a "magnet") 110a-1 that is located within the receptacle and that, by virtue of its size and shape, prevents additional magnets from being inserted into the receptacle.

Figure 20:
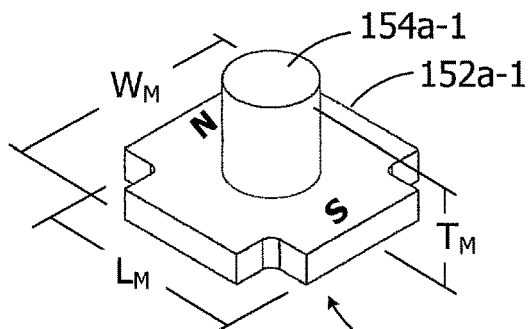
FIG. 20 is a perspective view of a magnet in accordance with one embodiment of a present invention.
Figure 21:
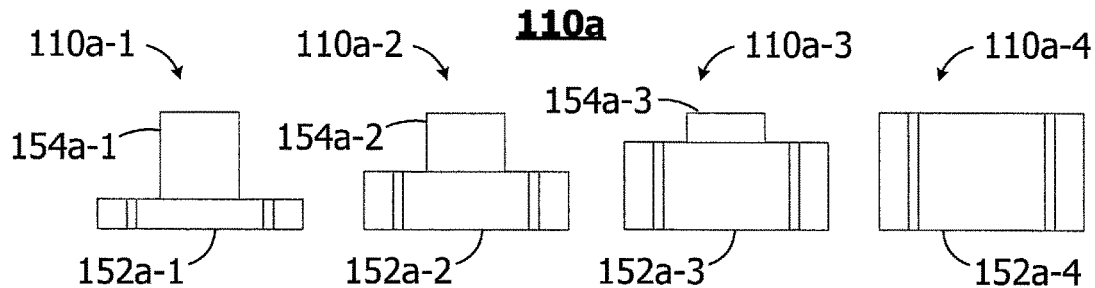
FIG. 21 is a side view of a magnet system in accordance with one embodiment of a present invention.

The magnet 110a-1 may be part of a magnet system that includes a plurality of similar-shaped magnets having different magnetic strengths. To that end, and referring to FIGS. 20 and 21, the exemplary multiple magnet system 110a also includes magnets 110a-2, 110a-3 and 110a-4. The magnets in the system 110a are similar in relevant shape and size, but have different magnetic strengths. Each of the magnets 110a-1 to 110a-4 in the magnet system 100a includes a respective magnetic member 152a-1 to 152a-4 that is configured for insertion into the similarly shaped receptacle 112. Each of the magnets 110a-1 to 110a-3 also includes a respective post 154a-1 to 154a-3, while the magnet 110a-4 consists solely of the magnetic member 152a-4. The magnetic members 152a-1 to 152a-4 may be formed from neodymium or any other suitable magnetic material. The posts 154a-1 to 154a-3 may be separate structures, formed from either magnetic or non-magnetic material, which are permanently secured to the associated magnetic member 152a-1 to 152a-3. Alternatively, magnets 110a-1 to 110a-3 may be one-piece structures where the magnetic members 152a-1 to 152a-3 and posts 154a-1 to 154a-3 of each magnet 110a-1 to 110a-3 is machined from a single piece of magnetic material. The posts 154a-1 to 154a-3 may be cylindrical-shaped (as shown) or may be some other shape.

In the exemplary implementation, the magnetic members 152a-1 to 152a-4 each have a cruciform shape that is similar to that of receptacle 112 and define the length $L_M$ and width $W_M$ of the respective magnets 110a-1 to 110a-4, which is the same from magnet to magnet. The thickness $T_M$ of the magnets 110a-1 to 110a-3 is equal to the combined thicknesses of the magnetic members 152a-1 to 152a-3 and the posts 154a-1 to 154a-3, while the thickness of magnet 110a-4 is simply the thickness of the magnetic member 152a-4. Although the length $L_M$ and width $W_M$ are the same in the illustrated embodiment, they may be different in other embodiments. The length $L_M$ and width $W_M$ of the magnets 110a-1 to 110a-4 may be identical to, or are at least substantially identical to (i.e., up to 3% less than), the length $L_R$ and width $W_R$ of the receptacle 112. The thickness $T_M$ may be at least 90% of the receptacle depth $D_R$ and, in the illustrated implementation, is at least substantially identical to depth $D_R$ (i.e., ±5%). As such, the free end of the posts 154a-1 to 154a-3 will be aligned with the receptacle top end 148, as will one end of the magnetic member 152a-4, when a magnet 110a-1 to 110a-4 is located within the receptacle 112, thereby preventing insertion of additional magnets. In those instances where the magnet thickness $T_M$ is greater than the receptacle depth $D_R$ (up to 10% greater), the inner surface of the cap 108 may have a small recess (not shown) that can accommodate the portion of the magnet that extends beyond the receptacle 112.

The strength of the magnets 110*a*-1 to 110*a*-4 may be varied by varying the relative thicknesses of the magnetic members 152*a*-1 to 152*a*-4 and posts 154*a*-1 to 154*a*-3 (including the lack of a post). For example, the magnetic strength of the magnet 110*a*-2 is greater than the magnet 110*a*-1. Although the overall thickness $T_M$ of the magnets 110*a*-1 and 110*a*-2 is the same, the thickness of the magnetic member 152*a*-2 is greater than the thickness of the magnetic member 152*a*-1, while the thickness of the post 154*a*-2 is less than the thickness of the post 152*a*-1.

The length of the posts 154*a*-1 to 154*a*-3 (as well as the lack thereof) also functions as indicia which identifies the relative strengths of the magnets 110*a*-1 to 110*a*-4. The longest post is indicative of the weakest magnet (i.e., magnet 110*a*-1) and the lack of a post is indicative of the strongest magnet (i.e., magnet 110*a*-4). Other types of strength representative indicia (e.g., numbers or color) may also be employed. Indicia indicative of the N-S magnetization direction (FIG. 20) may also be provided on the top and/or bottom surfaces of the magnetic members 152*a*-1 to 152*a*-4.

Figure 22:
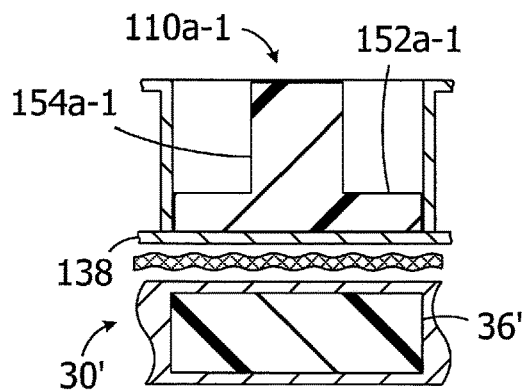
FIG. 22 is a simplified side, section view of portions of a cochlear implant and the headpiece illustrated in FIG. 18.
Figure 23:
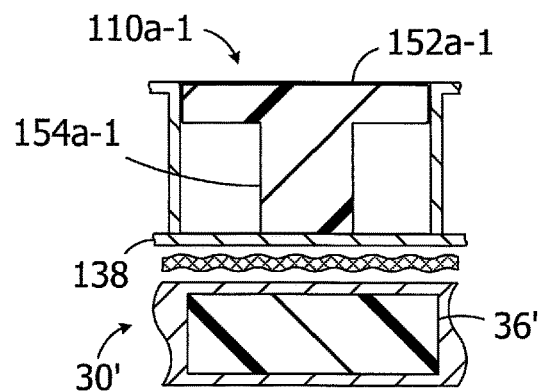
FIG. 23 is a simplified side, section view of portions of a cochlear implant and the headpiece illustrated in FIG. 18.
Figure 28:
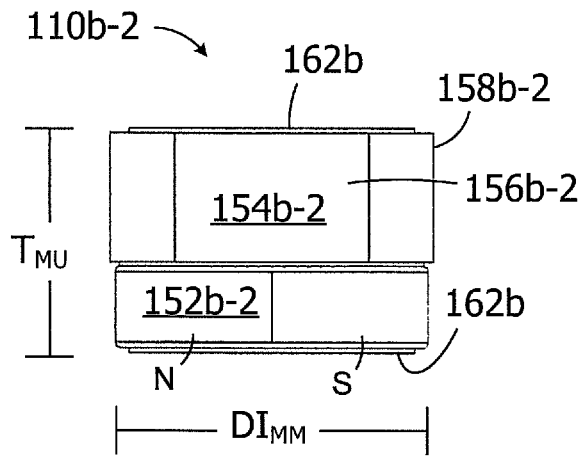
FIG. 28 is a side view of a magnet in accordance with one embodiment of a present invention.
Figure 29:
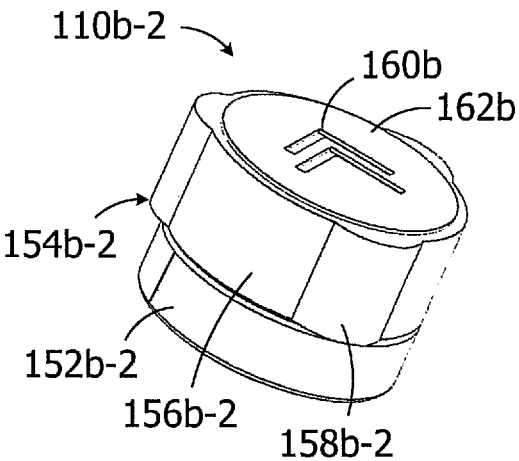
FIG. 29 is a perspective view of the magnet illustrated in FIG. 28.
Figure 30:
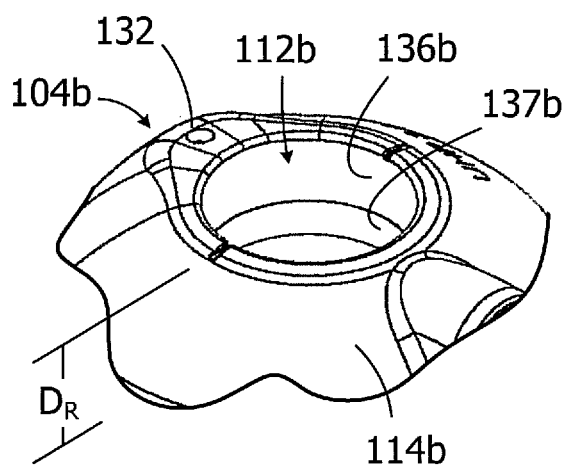
FIG. 30 is a perspective view of a portion of the headpiece illustrated in FIG. 24.
Figure 31:
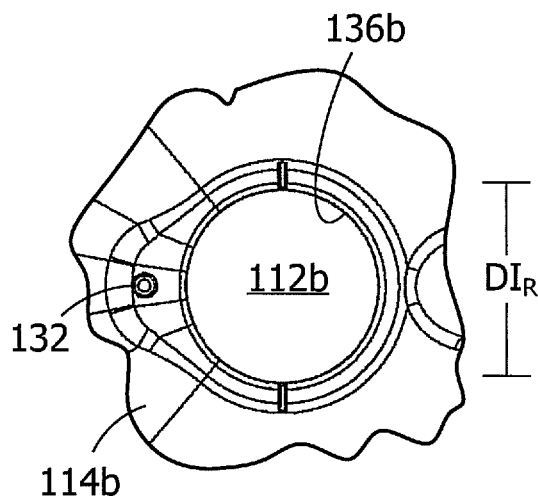
FIG. 31 is a top view of a portion of the headpiece illustrated in FIG. 24.

Here too, due to their respective configurations, the number of magnetic strength options provided by the exemplary headpiece 100*a* and magnet system 110*a* is greater than the number of magnets in the system. The magnets 110*a*-1 to 110*a*-3, each of which has a different strength, may be inserted with the magnetic member 152*a*-1 to 152*a*-3 facing the implant magnet 36' (e.g., magnetic member 152*a*-1 in FIG. 22) or with the associated post 154*a*-1 to 154*a*-3 facing the implant magnet (e.g., post 154*a*-1 in FIG. 23). Put another way, the magnets 110*a*-1 to 110*a*-3 may be inserted into the receptacle 112 in such a manner that the post 154*a*-1 to 154*a*-3 is between the associated magnetic member 152*a*-1 to 152*a*-3 and the bottom wall 138, or in such a manner that the post is not between the associated magnetic member and the bottom wall. The user can, therefore, select either of two possible magnetic member to implant magnet distances for each of the magnets 110*a*-1 to 110*a*-3 depending upon the insertion orientation of the magnet. The magnet 110*a*-4, which lacks a post, does not have this functionality. Accordingly, each of the magnets 110*a*-1 to 110*a*-3 is capable of creating two different magnetic attraction forces with the same implant magnet.

Another exemplary headpiece is generally represented by reference numeral 100*b* in FIGS. 24-27. The headpiece 100*b* may include a housing 102*b*, with a main portion 104*b* and a cover 106*b*, and a removable cap 108*b* that may be secured to the housing. A single headpiece magnet apparatus (also referred to herein as a "magnet") 110*b*-2 is located within a receptacle 112*b* that extends to the top wall 114*b* of the main portion 104*b*. The cap 108*b* keeps the magnet 110*b*-2 within the receptacle 112*b*, and can be removed and reattached so that the magnet can be removed and replaced. As is discussed in greater detail below with reference to FIGS. 28-35, the magnet 110*b*-2 and receptacle 112*b* are respectively configured in such a manner that the magnet may be fixed in any desired rotational orientation relative to the remainder of the headpiece. The magnet 110*b*-2, when fully inserted into the receptacle 112*b*, will prevent additional magnets (regardless of configuration) from being inserted into the receptacle. The magnet 110*b*-2 may also be part of a magnet system that includes a plurality of similar magnets having different magnetic strengths, as is described below with reference to FIGS. 36-38.

The internal volume of the exemplary housing 102*b* includes a microphone 116 and a printed circuit board (PCB) 118*b* which carries the microphone and various other headpiece electronic components on one other side. The other side of the PCB 118*b* includes an antenna 120 within an annular protective covering 122 (FIG. 27). In other implementations, the antenna may be carried by the cover 106*b*. The PCB 118*b* also includes an aperture 124*b* through which the receptacle 112*b* extends. A connector 126, such as a RF connector, is connected to the PCB 118*b* and extends through a tube 128*b* on the housing main portion 104*b*. The exemplary cap 108*b* has a hood 130 to accommodate the connector 126 and tube 128*b*. The housing 102*b* and cap 108*b* also include microphone ports 132 and 134 that are aligned with the microphone 116. A shield (not shown) may be positioned over the port 132 on the inner surface of the cap 108*b*.

In the illustrated implementation, the housing main portion 104*b* and cover 106*b* include respective annular walls 136*b* and 137*b* that together define the receptacle 112*b*. The housing cover 106*b* also includes a bottom wall 138*b*, which forms the bottom of the receptacle 112*b*, and an annular indentation 140 for the antenna's protective covering 122. The bottom surface of the bottom wall 138 may be concave or flat, and may include a plurality of protrusions 142. The housing 102*b* and cap 108*b* may be attached to one another with any suitable instrumentality. In the illustrated implementation, the housing main portion 104*b* also includes a plurality of latch indentations 144 that are engaged by a corresponding plurality of latches 146 on the cap 108*b* when the cap is positioned over the housing 102 in the manner illustrated in FIG. 24.

Figure 32:
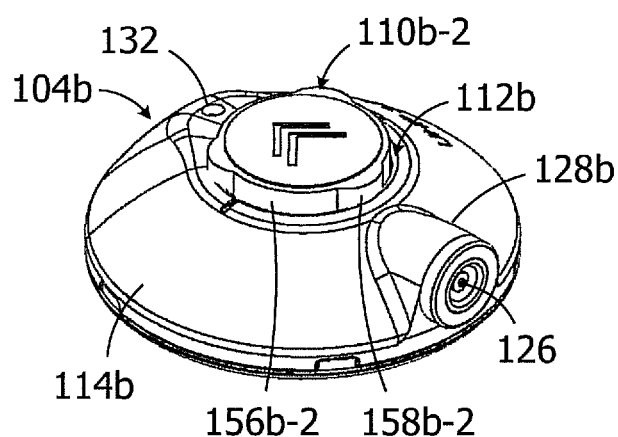
FIG. 32 is a perspective view of a portion of the headpiece illustrated in FIG. 24 prior to compression of the non-magnetic portion of the magnet.
Figure 33:
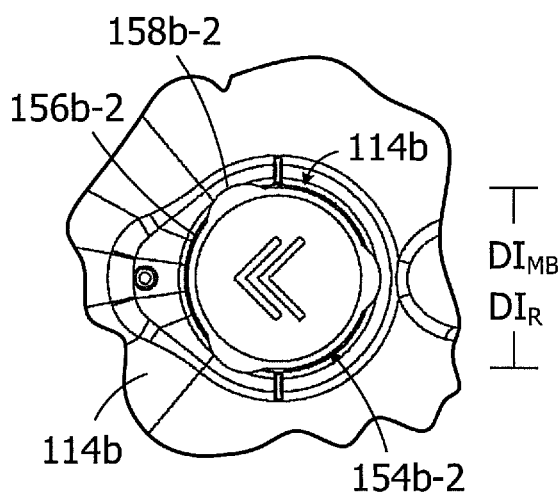
FIG. 33 is a top view of a portion of the headpiece illustrated in FIG. 24 prior to compression of the non-magnetic portion of the magnet.
Figure 34:
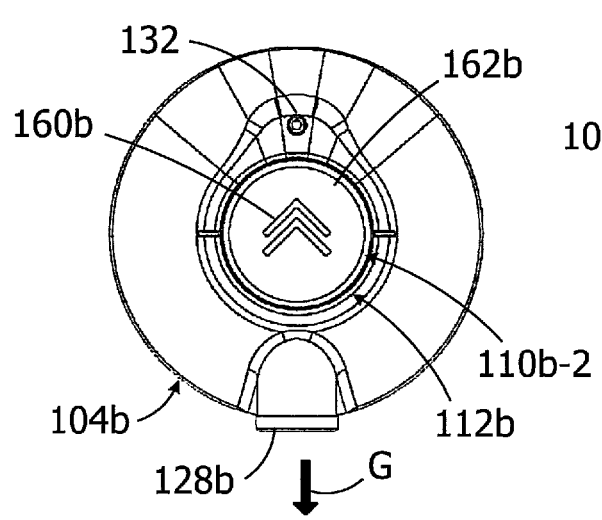
FIG. 34 is a top view of a portion of the headpiece illustrated in FIG. 24 after compression of the non-magnetic portion of the magnet.
Figure 35:
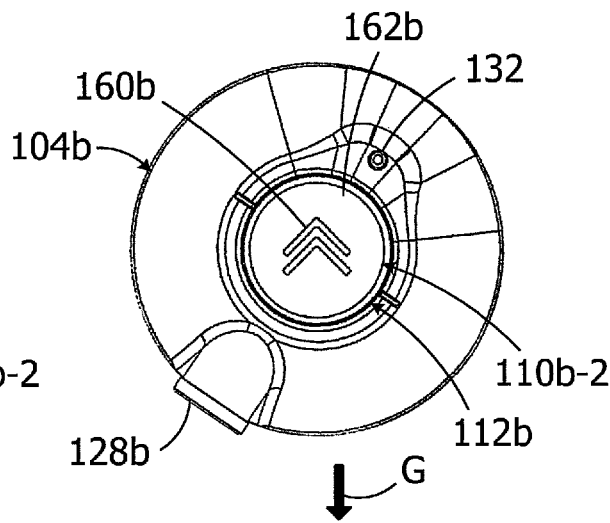
FIG. 35 is a top view of a portion of the headpiece illustrated in FIG. 24 after compression of the non-magnetic portion of the magnet.

Referring to FIGS. 28-31, the exemplary magnet 110*b*-2 is a two-part structure that includes a magnetic member 152*b*-2 and a non-magnetic member 154*b*-2 that may be permanently secured to the magnetic member. The magnetic member 152*b*-2 is disk-shaped, diametrically magnetized, and has a diameter $DI_{MM}$ that is identical to, or is at least substantially identical to, the receptacle diameter $DI_R$. The non-magnetic member 154*b*-2, which may be compressible and formed from foam or another compressible material, includes a disk-shaped main body 156*b*-2 and one or more projections 158*b*-2 that extend radially outward from the main body. The diameter $DI_{MB}$ of the main body 156*b*-2 of the compressible non-magnetic member 154*b*-2 is identical to, or is at least substantially identical to, the receptacle diameter $DI_R$. The uncompressed thickness $T_{MU}$ of the magnet 110*b*-2 is greater than the depth $D_R$. As such, when the magnet 110*b*-2 is placed into the receptacle 112*b* (with the magnetic member 152*b* closest to the housing cover 106*b*), a portion of each of the projections 158*b*-2 will extend beyond receptacle perimeter at the top of the receptacle and over the top wall 114, as shown in FIGS. 32 and 33. The non-magnetic member 154*b*-2 may then be compressed into the receptacle 112*b* (as shown in FIG. 34) with a finger or a tool, or by attaching the cover 108*b* to the housing 102*b*. Such compression will cause the non-magnetic member 154*b*-2 to press against the inner surface of the receptacle 112*b*, especially at the projections 158*b*-2, to create enough friction to maintain the magnet 112*b* within the receptacle and prevent the non-magnetic member from expanding back to its uncompressed state. The presence of the magnet 110*b*-2 in the receptacle 112*b* also prevents additional magnets (regardless of configuration) from being inserted into the receptacle, thereby preventing the unauthorized use of an additional magnet.

The exemplary magnet 110*b*-2 also includes indicia 160*b* that may be used to indicate the N-S direction of the associated diametrically magnetized magnetic member 152*b*-2 as well as the strength of the magnet relative to other magnets in the associated magnet system, as is described below with reference to FIGS. 36-38. In the illustrated implementation, the indicia 160*b* is in the form of one or more chevrons that point in the N (or S) direction. In those instances where the headpiece 100*b* is used in conjunction with a cochlear implant that includes a rotatable diametrically magnetized disk shaped magnet (e.g., implant 30' in FIG. 15 or one of the implants described in U.S. Pat. Pub. No. 2017/0239476), for example, indicia 160*b* the user will be able to align the N-S magnetization direction of the magnetic member 152*b*-2 with the gravitational direction G (FIG. 34). Moreover, because the magnet 110*b*-2 may be fixed in any desired rotational orientation about the axis A relative to the receptacle 112*b* and the remainder of the headpiece, the N-S magnetization direction of the magnetic member 152*b*-2 with the gravitational direction G in any instance where the connector 126 (which is within tube 128*b*) and associated cable do not point in the gravitational direction G (see, e.g., FIG. 35).

Figure 36:
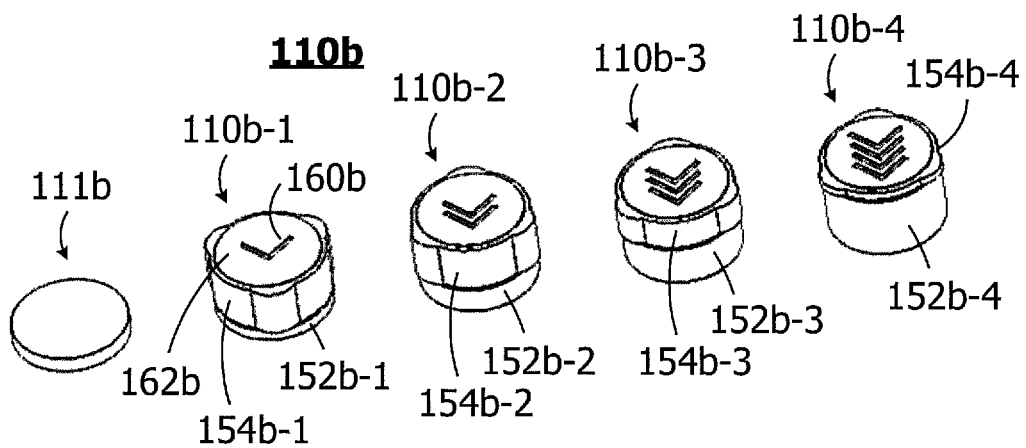
FIG. 36 is a perspective view of a magnet system in accordance with one embodiment of a present invention.
Figure 37:
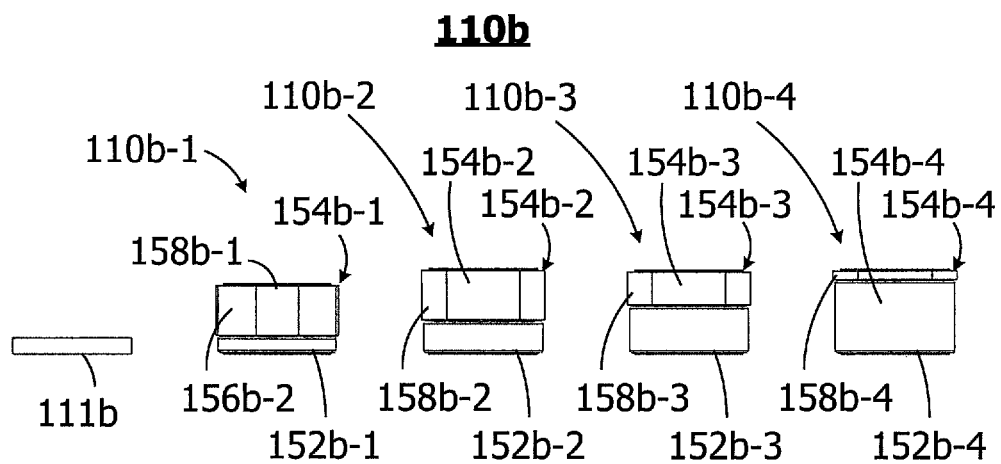
FIG. 37 is a side view of the magnet system illustrated in FIG. 36.
Figure 38:
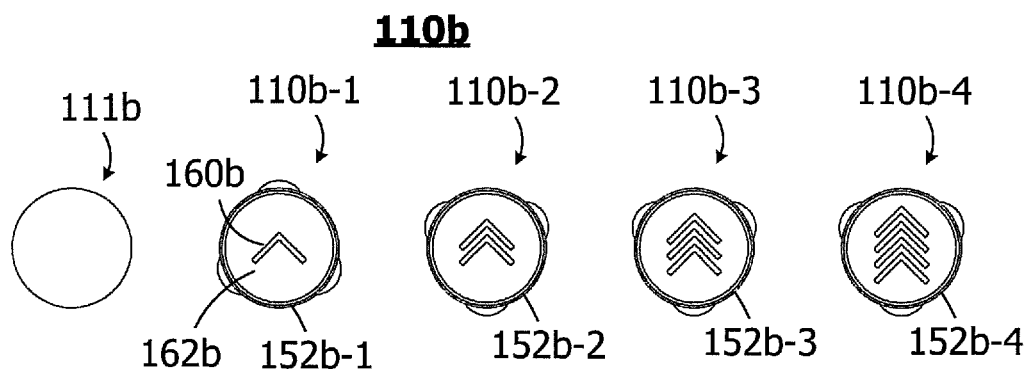
FIG. 38 is a bottom view of the magnet system illustrated in FIG. 36.

Turning to FIGS. 36-38, the exemplary magnet 110*b*-2 is one magnet in a multiple magnet system 110*b* that also includes magnets 110*b*-1, 110*b*-3 and 110*b*-4. The magnets in the system 110*b* are similar in shape and size, but have different magnetic strengths. The magnetic strength is varied from magnet to magnet by varying the sizes of the magnetic members and the compressible non-magnetic members. In particular, the magnets 110*b*-1 to 110*b*-4 are each two-part structures that each include a disk-shaped, diametrically magnetized magnetic member 152*b*-1 to 152*b*-4 and a compressible non-magnetic member 154*b*-1 to 154*b*-4 that is permanently secured to the associated magnetic member. The compressible non-magnetic members 154*b*-1 to 154*b*-4 each include a disk-shaped main body 156*b*-1 to 156*b*-4 and one or more projections 158*b*-1 to 158*b*-4 that extend radially outward from the main body. In some instances, a compressible spacer 111 (e.g., a foam spacer) may also be provided in the system 110*b*. The inner surface of the cap 108*b* may have a small recess (not shown) that can accommodate the portion of a magnet that extends beyond the receptacle 112*b*.

The respective uncompressed thicknesses $T_{MU}$ (FIG. 28) of the magnets 110*b*-1 to 110*b*-4 are greater than the receptacle depth $D_R$, but for the slightly shorter magnet 110*b*-1, while the diameters $DI_{MM}$ are the same. The respective thicknesses (and strengths) of the magnetic members increases from magnetic member 152*b*-1 to magnetic member 152*b*-4, while the uncompressed thicknesses of the non-magnetic members decreases from non-magnetic member 154*b*-1 to non-magnetic member 154*b*-4.

In the illustrated implementation, the number of chevrons 160*a* identifies the relative strengths of the magnets 110*b*-1 to 110*b*-4. A single chevron 160*b* is indicative of the weakest magnet (i.e., magnet 110*b*-1) and four chevrons are indicative of the strongest magnet (i.e., magnet 110*b*-4). Alternatively, or in addition, other types of strength representative indicia (e.g., numbers or color) may also be employed. The chevrons 160*a* (or other indicia) may also be provided on the top and bottom surfaces of the magnets 110*b*-1 to 110-4. The chevrons 160*b* or other indicia may, for example, be provided on adhesive labels 162*b* (as shown) or formed directly on the associated surfaces.

Figure 39:
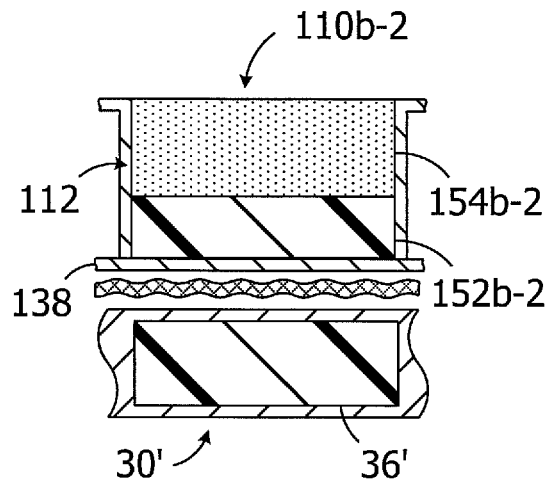
FIG. 39 is a simplified side, section view of portions of a cochlear implant and the headpiece illustrated in FIG. 24.
Figure 40:
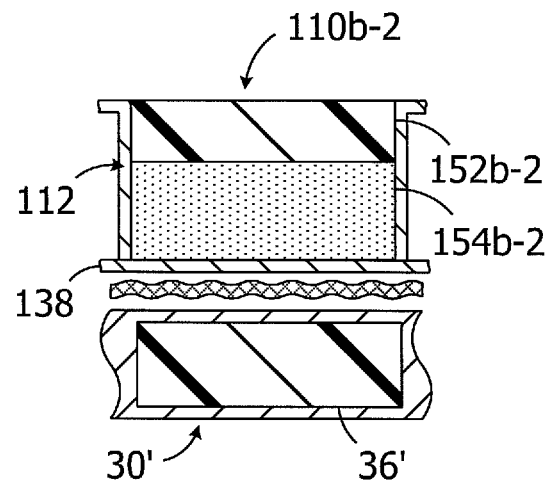
FIG. 40 is a simplified side, section view of portions of a cochlear implant and the headpiece illustrated in FIG. 24.

As described above in the context of magnet systems 110 and 110*a*, the number of magnetic strength options provided by the exemplary headpiece 100*b* and magnet system 110*b* is greater than the number of magnets in the system. The magnets 110*b*-1 to 110*b*-4, each of which has a different strength, may be inserted with the magnetic member 152*b*-1 to 152*b*-4 facing the implant magnet 36' (e.g., magnetic member 152*b*-2 in FIG. 39) or with the associated compressible non-magnetic member 154*b*-1 to 154*b*-4 facing the implant magnet (e.g., non-magnetic member 154*b*-2 in FIG. 40). Put another way, the magnets 110*b*-1 to 110*b*-4 may be inserted into the receptacle 112*b* in such a manner that the non-magnetic member 154-1 to 154-4 is between the associated magnetic member 152*b*-1 to 152*b*-4 and the bottom wall 138, or in such a manner that the non-magnetic member is not between the associated magnetic member and the bottom wall. The user can, therefore, select either of two possible magnetic member to implant magnet distances for each of the magnets 110*b*-1 to 110*b*-4 depending upon the insertion orientation of the magnet. Additionally, given the slightly lesser thickness of the magnet 110*b*-1, the compressible spacer 111*b* may be placed between the magnet 110*b*-1 and the bottom end of the reservoir 112*b* when the magnet 110*b*-1 is in either orientation. Accordingly, each of the magnets 110*b*-2 to 110*b*-4 is capable of creating two different magnetic attraction forces with the same implant magnet, while the magnet 110*b*-1 is capable of creating four different magnetic attraction forces with the same implant magnet.

Figure 41A:
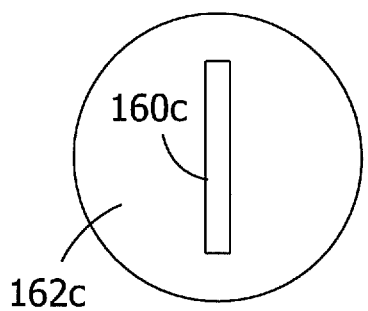
FIGS. 41A to 41C are top views showing various indicia examples.
Figure 41B:
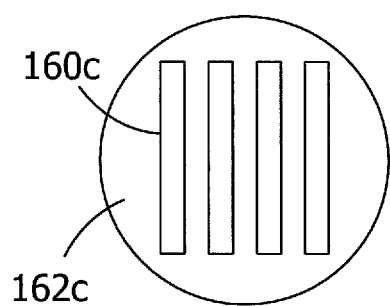
Figure 41C:
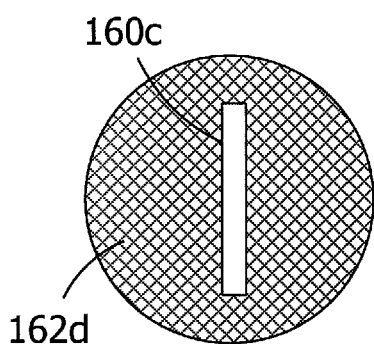

As noted above, the present magnet systems are not limited to any particular type of indicia. By way of example, but not limitation, the indicia may be in the form of elongate rectangles 160*c* (FIGS. 41A and 41B) that extend in the N-S magnetization direction. The number of elongate rectangles 160*c* will increase with magnetic strength. The rectangles 160*c* may be printed onto adhesive labels 162*c* (as shown) or formed directly onto the associated surface. Turning to FIGS. 41A and 41C, a single rectangle 160*c* that extends in the N-S magnetization direction may be used for each of the magnets in a magnet system, and color and/or texture may be used to indicate magnetic strength. For example, the colors white (label 162*c* in FIG. 41A), yellow, green and red (label 162*d* in FIG. 41C) may be employed.

Figure 42:
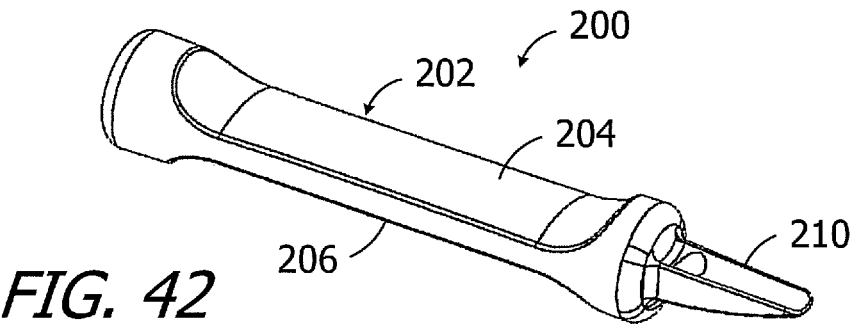
FIG. 42 is a perspective view of a tool in accordance with one embodiment of a present invention.
Figure 43:
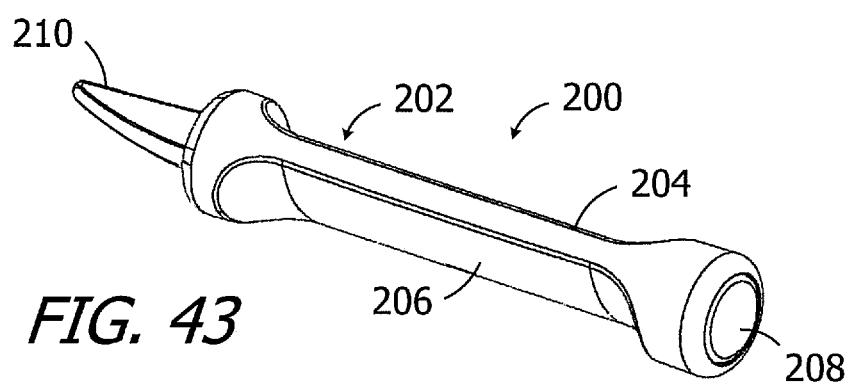
FIG. 43 is a perspective view of the tool illustrated in FIG. 42.

The present inventions also include tools that are configured to insert the above-described magnets into their associated headpieces and to remove the magnets from the headpieces. One exemplary tool is generally represented by reference numeral 200 in FIGS. 42 and 43. The exemplary tool 200 includes a handle 202 with indentations 204 and 206, a diametrically magnetized magnet 208, and a wedge 210. The tool 200 may be used to, for example, insert the magnet 110*b*-2 into the headpiece 100*b* (FIGS. 24 and 25) by placing the magnet 208 against the end of magnet 110*b*-2 that will be at the top of the receptacle. Although this may be the end formed from the compressible material of the non-magnetic member 154*b*-2, the attraction between the magnetic member 152*b*-2 and the magnet 208 will be sufficient to secure the magnet 110*b*-2. The tool 200 may then be used to push the magnet 110*b*-2 into the recess 112*b* and compress the non-magnetic member 154*b*-2 completely into the recess. The tool 200 may be separated from the magnet 110*b*-2 by moving the magnet 208 laterally across the top edge of the recess 112*b*. The tool 200 may also be used to remove the magnet 110*b*-2 from the headpiece 100*b* by placing magnet 208 over the open end of the recess 112*b* near or against the exposed surface of the magnet. The magnetic attraction between the magnet 208 and the magnetic member 152*b*-2 will cause the magnet 110*b*-2 to be pulled out of the receptacle 112*b* as the tool 200 is moved away from the receptacle in the axial direction. The tool 200 may also be used to insert and/or remove the other magnets described herein in substantially the same way. The wedge 210 may be used to remove the cap 108 from the housing 102. In particular, the wedge 210 may be pressed between the housing tube 128 and the cap hood 130, and then pivoted to force the latches 146 out of the indentations 144.

Figure 44:
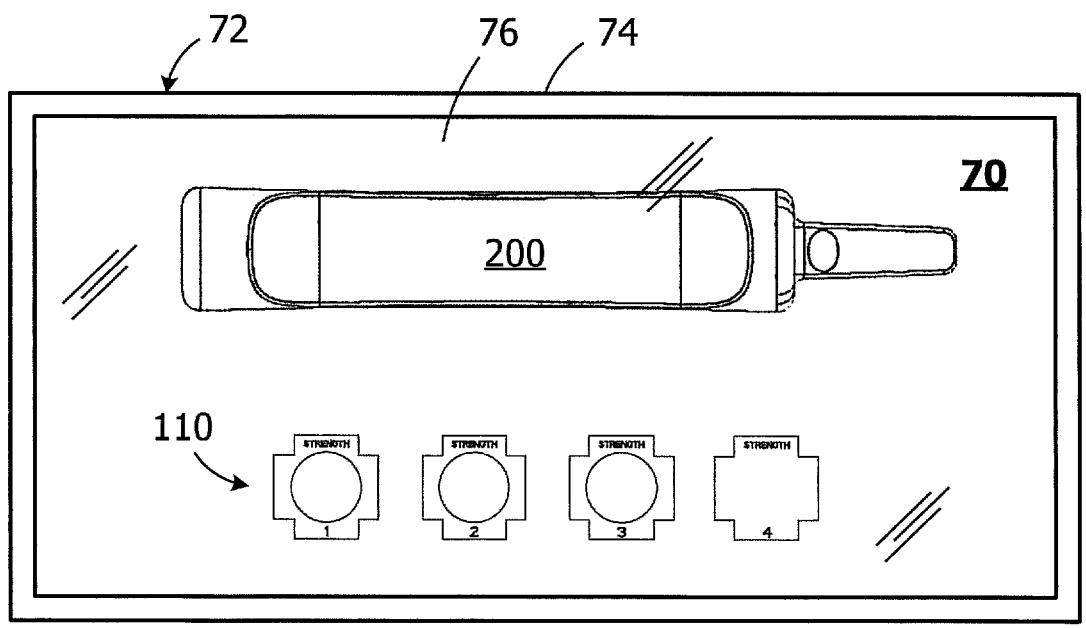
FIG. 44 is a top view of a magnet kit in accordance with one embodiment of a present invention.

As illustrated for example in FIG. 44, the exemplary magnet system 100 (or 110*a* or 110*b*) may be provided as part of a kit 70 to, for example, audiologists so that the most appropriate magnet may be selected during the fitting process. Here, the magnets 110-1 to 110-4 of the system 100 may be located within packaging 72, which in the illustrated implementation includes a box or other enclosure 74 with a cover 76, for shipping and storage. The cover 76 may be transparent, as shown, or opaque. The tool 200 may in some instances be provided within the packaging 72 as part of the kit 70. In other implementations, the kit may also include the headpiece itself. Here, a magnet system (e.g., the magnet system 110) may be provided in the same packing as the headpiece (e.g., the headpiece 100). The tool 200 may also be provided in the same packaging as the magnet system and headpiece.

Figure 45:
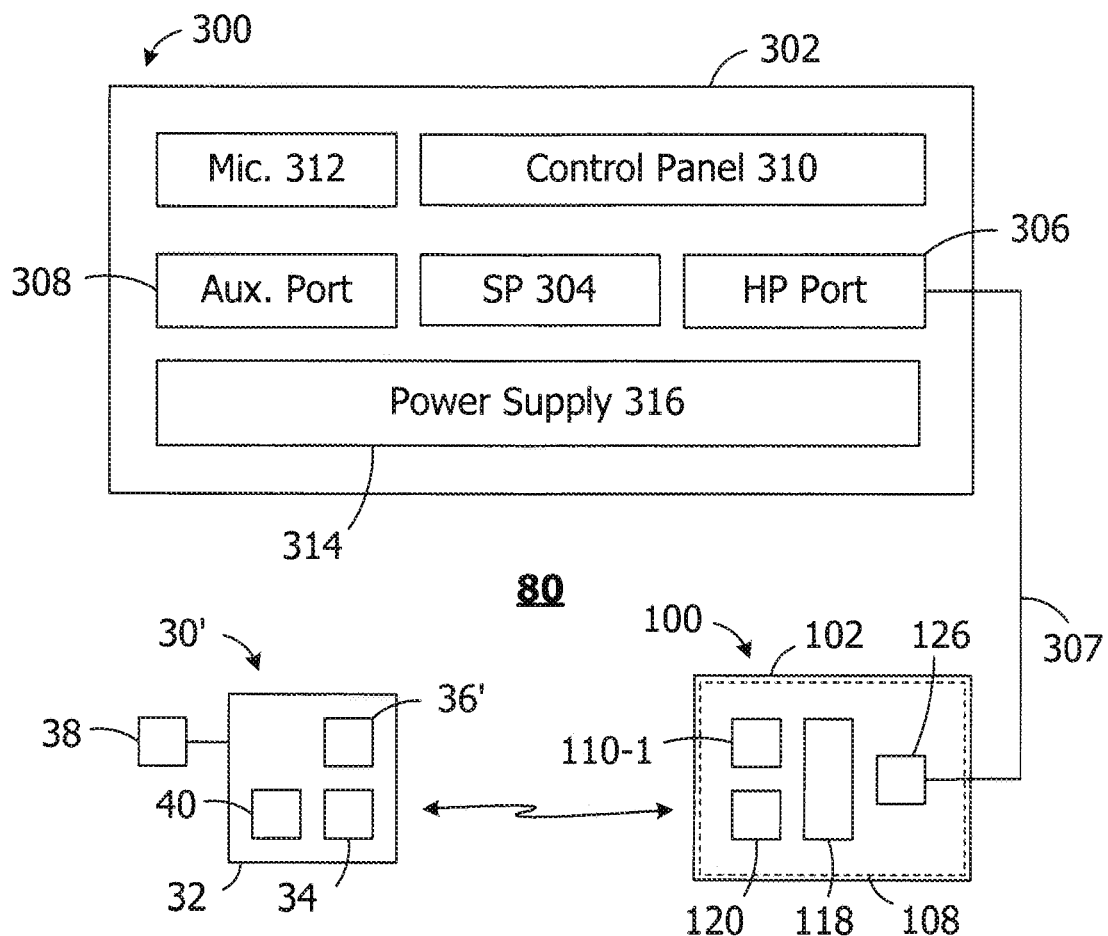
FIG. 45 is a block diagram of an ICS system in accordance with one embodiment of a present invention.

With respect to exemplary ICS systems that include the present headpieces, the exemplary ICS system 80 illustrated in FIG. 45 includes the cochlear implant 30', a headpiece 100 (or 100*a* or 100*b*), and a sound processor 300, such as a body worn sound processor or a behind-the-ear sound processor.

The exemplary sound processor 300 is a body worn sound processor that includes a housing 302 in which and/or on which various components are supported. Such components may include, but are not limited to, sound processor circuitry 304, a headpiece port 306 that may be connected to the headpiece 100 by a cable 307, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data.

During use, one of the above-described headpiece magnets (e.g., 110-1) will be attracted to the implant magnet 36', thereby aligning the headpiece antenna 120 with the implant antenna 34. The stimulation data and, in many instances power, is supplied to the headpiece 100, which transcutaneously transmits the stimulation data, and in many instances power, to the cochlear implant 30' by way of a wireless link between the antennas. In at least some implementations, the cable 307 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the headpiece microphone 116 may be omitted in some instances.

It should be noted that the present magnets and magnet systems may be employed in ICS systems which are configured such that all of the components (e.g., the battery, the microphone, the sound processor, and the antenna coil) are carried within a single headpiece. One example of such a system is disclosed in U.S. Pat. Pub. No. 2010/0046778, which is entitled "Integrated Cochlear Implant Headpiece" and incorporated herein by reference in its entirety.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant headpiece for use with a cochlear implant, the cochlear implant headpiece comprising:
    a housing including a bottom wall that faces the cochlear implant and a magnet receptacle and defining a receptacle axis that extends through the magnet receptacle in a direction perpendicular to the bottom wall, the magnet receptacle including an open top end and a closed bottom end defined by the bottom wall and defining a non-circular shape in a plane perpendicular to the receptacle axis;
    a headpiece magnet, defining the non-circular shape in a plane perpendicular to the receptacle axis and defining a N-S magnetization direction, removably located within the magnet receptacle such that the receptacle axis passes through the headpiece magnet; and
    a headpiece antenna carried by the housing;
    wherein the non-circular shape of the magnet receptacle and the headpiece magnet is such that the headpiece magnet may be removably located within the magnet receptacle at first and second rotationally offset orientations relative to the magnet receptacle and the N-S magnetization direction of the headpiece magnet in the first rotational orientation intersects the N-S magnetization direction of the headpiece magnet in the second rotational orientation.

2. A cochlear implant headpiece as claimed in claim 1, wherein
    the headpiece magnet is not rotatable relative to the magnet receptacle when located within the magnet receptacle.

3. A cochlear implant headpiece as claimed in claim 1, wherein
    the magnet receptacle defines a receptacle depth; and
    the headpiece magnet defines a magnet thickness that is at least 90% of the receptacle depth.

4. A cochlear implant headpiece as claimed in claim 3, wherein
    the magnet thickness is at least equal to the receptacle depth.

5. A cochlear implant headpiece as claimed in claim 1, wherein
    the headpiece magnet defines a N-S magnetization direction that is perpendicular to the receptacle axis.

6. A cochlear implant headpiece as claimed in claim 5, further comprising:
    a headpiece cable connector associated with the housing;
    wherein the respective configurations of the magnet receptacle and the headpiece magnet are so that the N-S magnetization direction may be aligned with headpiece cable connector.

7. A cochlear implant headpiece as claimed in claim 1, further comprising:
    a cap configured to be mounted on the housing and to cover the magnet receptacle when mounted on the housing.

8. A cochlear implant headpiece as claimed in claim 1, wherein
the headpiece magnet includes a magnetic member defining the non-circular shape in a plane perpendicular to the receptacle axis and a non-magnetic member defining the non-circular shape in a plane perpendicular to the receptacle axis.

9. A cochlear implant headpiece as claimed in claim 8, wherein
the non-magnetic member is permanently secured to the magnetic member.

10. A cochlear implant headpiece as claimed in claim 8, wherein the headpiece magnet defines a first headpiece magnet having a first magnetic strength, the cochlear implant headpiece further comprising:
a second headpiece magnet, insertable into the magnet recess in place of the first headpiece magnet, defining the non-circular shape in a plane perpendicular to the receptacle axis and having a second magnet strength that is greater than the first magnetic strength.

11. A cochlear implant headpiece as claimed in claim 10, wherein
the magnetic members and the non-magnetic members of the first and second magnets define respective thicknesses;
the thickness of the magnetic member of the second magnet is greater than the thickness of the magnetic member of the first magnet; and
the thickness of the non-magnetic member of the second magnet is less than the thickness of the non-magnetic member of the first magnet.

12. A cochlear implant headpiece for use with a cochlear implant, the cochlear implant headpiece comprising:
a housing including a bottom wall that faces the cochlear implant and a magnet receptacle and defining a receptacle axis that extends through the magnet receptacle in a direction perpendicular to the bottom wall, the magnet receptacle including an open top end and a closed bottom end defined by the bottom wall and defining a cruciform shape in a plane perpendicular to the receptacle axis;
a headpiece magnet, defining the cruciform shape in a plane perpendicular to the receptacle axis and defining a N-S magnetization direction, removably located within the magnet receptacle such that the receptacle axis passes through the headpiece magnet; and
a headpiece antenna carried by the housing.

13. A cochlear implant headpiece for use with a cochlear implant, the cochlear implant headpiece comprising:
a housing including a bottom wall and a magnet receptacle and defining an axis that extends through the magnet receptacle in a direction perpendicular to the bottom wall, the magnet receptacle defining a non-circular shape in a plane perpendicular to the axis;
a headpiece magnet removably located within the magnet receptacle and including a magnetic member defining the non-circular shape in a plane perpendicular to the axis and a non-magnetic member defining the non-circular shape in a plane perpendicular to the axis; and
a headpiece antenna carried by the housing;
wherein the headpiece magnet and the magnet receptacle are respectively configured so that the headpiece magnet may be inserted into the magnet receptacle in a first orientation where the non-magnetic member is between the magnetic member and the housing bottom wall and in a second orientation where the non-magnetic member is not between the magnetic member and the housing bottom wall.

14. A cochlear implant headpiece for use with a cochlear implant, the cochlear implant headpiece comprising:
a housing including a bottom wall and a magnet receptacle and defining an axis that extends through the magnet receptacle in a direction perpendicular to the bottom wall, the magnet receptacle defining a non-circular shape in a plane perpendicular to the axis;
a headpiece magnet, including a magnetic member defining the non-circular shape in a plane perpendicular to the axis and a post extending from the magnetic member, removably located within the magnet receptacle; and
a headpiece antenna carried by the housing.

15. A cochlear implant headpiece as claimed in claim 14, wherein
the post is formed from magnetic material.

16. A cochlear implant headpiece as claimed in claim 14, wherein
the headpiece magnet and the magnet receptacle are respectively configured so that the headpiece magnet may be inserted into the magnet receptacle in a first orientation where the post is between the magnetic member and the housing bottom wall and in a second orientation where the post is not between the magnetic member and the housing bottom wall.

17. A cochlear implant headpiece as claimed in claim 14, wherein the headpiece magnet defines a first headpiece magnet having a first magnetic strength, the cochlear implant headpiece further comprising:
a second headpiece magnet, insertable into the magnet recess in place of the first headpiece magnet, defining the non-circular shape in a plane perpendicular to the axis and having a second magnet strength that is greater than the first magnetic strength.

18. A cochlear implant headpiece as claimed in claim 17, wherein
the magnetic members and the posts of the first and second magnets define respective thicknesses;
the thickness of the magnetic member of the second magnet is greater than the thickness of the magnetic member of the first magnet; and
the thickness of the post of the second magnet is less than the thickness of the post of the first magnet.

* * * * *